(12) United States Patent
Owen et al.

(10) Patent No.: US 10,730,999 B2
(45) Date of Patent: Aug. 4, 2020

(54) DENDRIMER-DRUG CONJUGATES

(71) Applicant: Starpharma Pty Ltd, Abbotsford, Victoria (AU)

(72) Inventors: David James Owen, Kew (AU); Pauline Stanislawski, Pascoe Vale (AU); Michael Giannis, Point Cook (AU); Oliver Bernhard, Dorfprozelten (DE)

(73) Assignee: Starpharma Pty Ltd, Victoria (AU)

( * ) Notice: Subject to any disclaimer, the term of this patent is extended or adjusted under 35 U.S.C. 154(b) by 0 days.

(21) Appl. No.: 15/315,690

(22) PCT Filed: Jun. 5, 2015

(86) PCT No.: PCT/AU2015/050312
§ 371 (c)(1),
(2) Date: Dec. 1, 2016

(87) PCT Pub. No.: WO2015/184510
PCT Pub. Date: Dec. 10, 2015

(65) Prior Publication Data
US 2017/0189543 A1      Jul. 6, 2017

(30) Foreign Application Priority Data

Jun. 6, 2014   (AU) ............................. 2014902169

(51) Int. Cl.
| | | |
|---|---|---|
| *A61K 38/28* | (2006.01) | |
| *A61K 38/26* | (2006.01) | |
| *C08G 65/333* | (2006.01) | |
| *C08G 69/48* | (2006.01) | |
| *C08G 69/10* | (2006.01) | |
| *A61K 47/64* | (2017.01) | |
| *C08G 69/40* | (2006.01) | |
| *C08L 101/00* | (2006.01) | |
| *C08G 83/00* | (2006.01) | |
| *A61K 47/60* | (2017.01) | |

(52) U.S. Cl.
CPC .......... *C08G 65/3332* (2013.01); *A61K 38/26* (2013.01); *A61K 38/28* (2013.01); *A61K 47/60* (2017.08); *A61K 47/64* (2017.08); *C08G 69/10* (2013.01); *C08G 69/40* (2013.01); *C08G 69/48* (2013.01); *C08G 83/003* (2013.01); *C08L 101/00* (2013.01)

(58) Field of Classification Search
CPC ............................... A61K 38/26; A61K 38/28
See application file for complete search history.

(56) References Cited

U.S. PATENT DOCUMENTS

2010/0136614 A1   6/2010   Luo et al.

FOREIGN PATENT DOCUMENTS

| DE | 10041559 | 3/2002 |
|---|---|---|
| WO | 2007/048190 | 5/2007 |
| WO | 2007082331 | 7/2007 |
| WO | 2008017122 | 2/2008 |
| WO | 2008017125 | 2/2008 |
| WO | 2011/140376 | 11/2011 |
| WO | 2012/167309 | 12/2012 |
| WO | 2014/036323 | 3/2014 |
| WO | 2015/035446 | 3/2015 |

OTHER PUBLICATIONS

Kaminskas, L. M. et al., (2008) "The impact of molecular weight and PEG chain length on the systemic pharmacokinetics ofPEGylated poly l-lysine dendrimers" Molecular pharmaceutics, 5(3):449-463.
Kaminskas, L. M. et al., (2014) Pulmonary administration of a doxorubicin-conjugated dendrimer enhances drug exposure to lung metastases and improves cancer therapy. Journal of Controlled Release, 183:18-26.
International Search Report of Application PCT/AU2015/050312 dated Oct. 2, 2015.
Supplementary European Search Report of Application EP 15 803 996.6 dated Oct. 17, 2017.
Written Opinion of Application PCT/AU2015/050312 dated Oct. 2, 2015.

*Primary Examiner* — Gyan Chandra
(74) *Attorney, Agent, or Firm* — Rudy J. Ng; Carol L. Francis; Bozicevic, Field & Francis LLP

(57) ABSTRACT

The present invention generally relates to macromolecules of dendrimer-drug conjugates. In particular, the invention relates to macromolecules comprising a pharmaceutically active agent, such as a protein or peptide, attached to a core of a dendrimer derived from branched building units, such as lysine or lysine analogues. The invention also relates to the synthesis of the dendrimers and macromolecules, and the use of such macromolecules, particularly in therapeutic applications, and pharmaceutical compositions comprising them.

32 Claims, 5 Drawing Sheets

DENDRIMER-DRUG CONJUGATES

FIELD

The present invention generally relates to macromolecules of dendrimer-drug conjugates. In particular, the invention relates to macromolecules comprising a pharmaceutically active agent, such as a protein or peptide, attached to a core of a dendrimer derived from branched building units, such as lysine or lysine analogues. The invention also relates to the synthesis of the dendrimers and macromolecules, and the use of such macromolecules, particularly in therapeutic applications, and pharmaceutical compositions comprising them.

BACKGROUND

Drug candidates commonly fail to complete the development process in clinical trials because their physical properties (particularly solubility) make them difficult to formulate, or because of a poor therapeutic index that leads to toxic effects during the high drug concentrations that occur just after dosing. Other short comings include poor absorption, poor bioavailability, instability, systemic side effects due to an inability to target the drugs, and the inability to control their biodistribution, metabolism and renal or hepatic clearance once administered. Current products on the market can also be improved with regard to such issues. Additionally, the modification of known compounds to improve pharmacokinetic or pharmacodynamic properties or reduce unwanted side effects reduces the risks and cost associated with development of a new drug candidate.

Many peptides of therapeutic interest, such as hormones, soluble receptors, cytokines, enzymes etc are ineffective or inconvenient to administer as long acting drug candidates because of their short half-life and need for frequent repeat dosing. Short half-life is the result of too rapid clearance by the kidneys or liver or proteolytic degradation or immune clearance. There is a need for a delivery mechanism that prolongs half-life while maintaining effective activity.

A number of approaches have been tried to modify a pharmaceutical compound's pharmokinetic profile including the formulation of the pharmaceutical agent in a liposome, micellar or polymeric micelle formulation, as well as covalent attachment of the pharmaceutical agent to a hydrophilic polymer backbone, to improve stability and protect against proteolytic activity or immunoreactivity. Polyethylene glycol (PEG) has been used to attempt to improve half-life of proteins. High molecular weight (MW) PEG conjugated to proteins have been on the market for many years and evidence has recently been found of accumulation of these high MW PEG molecules over time in the kidneys and the choroidal plexus, which is a serious concern for chronic use conditions. These long chain high MW PEG can also make solutions excessively viscose and mask pharmaceutical activity, leading to substantially reduced efficacy. Further, it can be difficult to control PEG size, introducing variability into the finished product. Such variability reduces effectiveness and can impede regulatory approval. Low MW PEG generally has not provided adequate bulk or shielding to achieve the desired half-life improvement.

In spite of the extensive use of PEG for three decades now, there is no general consensus on what is the optimum coverage-density, conformation and molecular weight combination for a given carrier and application (J.-M. Rabanel et al./Journal of Controlled Release 185 (2014) 71-87). Controlling nanoparticle surface properties is a challenging task due to the many constrains that are involved in the design of a particle surface: long circulation time, low non-specific cellular uptake and active targeting have conflicting requirements in terms of surface properties. Target recognition and docking of ligand molecules located at the surface of a PEGylated particle are dependent on the density and thickness of the PEG and the positioning of the ligand.

Maintaining good glucose control has been shown to reduce diabetic complications such as retinopathy, neuropathy and nephropathy, as well as minimise hypoglycaemic events. However, many diabetics find it difficult to achieve good control in part because of compliance issues associated with frequent insulin injections, and the challenges of maintaining steady levels of basal insulin. Ideally injectable basal insulin would correlate to hepatic glucose output, maintain stable plasma glucose both fasting and between meals and prevent ketoacidosis (in T1DM). Daily basal insulin analogs, such as Lantus, Levimir and Tresiba have radically improved the way diabetics manage basal insulin levels, but there is a need to further reduce the frequency of injections and improve the pharmacokinetics of basal insulin to minimise likelihood of hypoglycaemia and other complications.

Currently available basal insulin replacement therapies are deficient in one or more clinically important aspects. For example the basal insulin analog, insulin detemir, possess a duration of activity that is insufficient to provide basal glucose control for a full day when administered daily. Furthermore, the inadvertent omission or delay of a single injection can lead to significant increase in "peak-to-trough" levels of the drug resulting in impaired glucose control. The insolubility mechanisms to prolong insulin release, e.g., the in vivo precipitation of insulin glargine or injection site multihexamers of degludec, increase intra-injection variability resulting in increased variability in the dose-response profile, and the acidity of glargine may cause pain on injection. Some insulin preparations require mixing to insure product uniformity, have increased intra-subject variability, and tend to peak rather than provide an ideal near "flat" pharmacodynamic profile (low peak to trough variations, $C_{max}$ to $C_{min}$) necessary to maintain steady basal insulin. The half-life profiles of these daily insulin preparations can be inadequate to provide daily dosing in some patients and twice daily dosing is required for good glucose control. Additionally, some modern basal insulin analogues are not readily mixable with rapid- or immediate-acting insulin formulations. For patients another unpleasant side effect is weight gain, which is commonly experienced with existing basal insulins. Currently available insulin replacement therapies are deficient in one or more clinically important aspects. For example, daily dosing of long-acting basal insulin formulations, such as detemir often do not provide the required basal glucose control for a full day. The loss of activity results in insufficient control and/or hyperglycemia. Furthermore, the omission of a single injection of the current therapies can lead to significant increase in "peak-to-trough" levels of the drug resulting in impaired glucose control. Many current long acting insulin formulations rely on an insoluble state to protract insulin payout. Also some of these products require mechanical mixing to insure product uniformity. Such strategies result in inherently less accurate dosing due to increased intra-injection variability, as well as intra-subject variability. The ultimate result being an increase in the variability in the dose-response profile and result in less than adequate control of blood glucose and a greater susceptibility to life-threatening hypoglycemic episodes. Further, current long acting insulin formulations tend to peak rather than provide an ideal "flat" pharmacodynamic profile necessary to maintain optimal fasting blood glucose for an extended period of time between meals. Clearly, there still exists a critical need for long-lasting insulins that are better suited for basal insulin replacement regimens. In particular, soluble basal insulins that are mixable with prandial insulin formulations, have extended timeaction profiles (i.e., able to adequately control blood glucose levels with an once-daily or less frequent injection), flatter activity, pharmacokinetic profiles (i.e., lower "peak-to-trough" ratios), reduced intra-patient variability (i.e., more predictable time-action profile translating into reduced incidence of hypoglycemia and/or weight gain) and/or lesser injection site irritation or pain upon injection are needed.

A number of patents relate to the conjugation of insulin to PEG, WO02/094200, US 2003-0229010. LY2605541, a construct made from a fast acting insulin analogue conjugated to PEG (~20 kDa), is in clinical trials (Hansen R J, et al. ADA 2012 abstract 896-P). WO 2006/079641 (novo nordisk) provides small dendrimers conjugated to insulin for pulmonary administration, with a short half-life. Pegylated insulin in PLGA microparticles have shown reduced efficacy, injection site reactions and unwanted burst like release.

In patients with type 2 diabetes, marked obesity, and insulin resistance, total daily insulin doses of 200 to 300 units are often required of which half may be basal insulin. It is desirable to concentrate insulin into a small volume to minimise injection site discomfort or multiple injections. High concentrations of insulin can be difficult to handle and deliver due to high viscosity, precipitation, and side reactions due to disulphide shuffling, from insulin forced into close contact. Similarly, insulin can be highly sensitive to heat and mechanical forces, which can result in precipitation.

Dendrimers are a special class of dendritic polymer with well controlled branched structures that are characterized by higher concentrations of functional moieties per unit of molecular volume than ordinary polymers. (Fréchet and Tomalia "Dendrimers and other Dendritic Polymers", Wiley and Sons, New York, 2002). Dendrimers offer a high degree of branching, multivalency, globular architecture and well-defined structure and molecular weight. The potential utility of dendritic polymers both as drug delivery vectors and pharmaceutical actives has received increasing interest in recent years.

However, it is still a challenge to prepare well defined dendrimers that circulate in the blood long enough to accumulate at target sites, but that maintain activity. Kaminskas et al (mol. pharm. 2008, VOL. 5, NO. 3, 449-463) describe pegylated dendrimers without pharmaceutical activity delivered i.v. with increased half-life, in normal rats.

An important consideration in the design of a complex compound is the cost of manufacture. A smaller or simpler construct may be more cost efficient to manufacture than a larger construct. Reducing complexity and size of a macromolecule while maintaining efficacy is highly desirable.

It has surprisingly been found that, the pharmacokinetic profile or half-life of a protein or peptide may be significantly improved, without adversely affecting efficacy, by using a pegylated dendritic macromolecule.

The reference in this specification to any prior publication (or information derived from it), or to any matter which is known, is not, and should not be taken as an acknowledgment or admission or any form of suggestion that that prior publication (or information derived from it) or known matter forms part of the common general knowledge, in Australia or any other country, in the field of endeavour to which this specification relates.

SUMMARY

The present invention relates to a macromolecule comprising a dendrimer having a core moiety with two or more building units and at least one pharmacokinetic modifier attached to the outermost layer of building units of the dendrimer, wherein a pharmaceutically active agent is attached to the core moiety. In particular, there is provided a dendrimer comprising a core moiety and one or more layers of lysine or lysine analogue building units wherein the dendrimer has a pharmaceutically active agent attached to the core moiety (e.g. via a linker) and at least one pharmacokinetic modifier attached to the outermost layer of building units. In one embodiment, the pharmaceutically active agent is a protein or polypeptide. In another embodiment, the pharmacokinetic profile of the pharmaceutically active agent can be improved when attached to the core moiety of the dendrimer.

In one aspect, there is provided a macromolecule of Formula I:

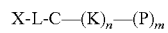

$$X\text{-}L\text{-}C\text{—}(K)_n\text{—}(P)_m \qquad \text{Formula I}$$

X represents a pharmaceutically active agent;

L represents a linker group;

C represents a core moiety having at least three functional groups each separately for attachment to L and at least two building units K;

K represents a building unit having at least two branching points for attachment to a pharmacokinetic modifier P or another building unit K;

n represents the total number of building units, and is a function of the number of generations and the extent of branching of the building units;

P represents a pharmacokinetic modifier;

m represents the number of surface pharmacokinetic modifiers.

In one embodiment, X is protein or peptide. In another embodiment, X is insulin or an insulin analogue.

C may be a core moiety comprising three functional groups each separately for attachment to L and at least two building units K. In some embodiments the functional group comprises a reactive nitrogen moiety. In one embodiment, C may be a di-$C_{1-10}$alkylenetriamine, for example dipropylene triamine.

L may be PEG. K may be a building unit of lysine or a lysine analogue. P may be PEG.

In another aspect, there is provided a macromolecule of Formula I:

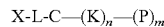

$$X\text{-}L\text{-}C\text{—}(K)_n\text{—}(P)_m \qquad \text{Formula I}$$

wherein

X represents a pharmaceutically active agent selected from the group consisting of insulin or an insulin analog GLP or a GLP analog or receptor agonist, and GIP or a GLP analog;

L represents a linker selected from the group consisting of polyethylene glycol (PEG), polypropylene glycol, polyaryls, peptides, alkyl and alkenyl chains, and saccharides (mono, oligo and poly);

C represents a core moiety having at least three functional groups each separately for attachment to L and attachment to at least two building units K, and wherein C is selected from a diamino or triamino moiety;

K represents a lysine or a lysine analog building unit having at least two branching points for attachment to a pharmacokinetic modifier P or another building unit K;

n is an integer from 14 and 126 and represents the total number of building units, and is a function of the number of generations and the extent of branching of the building units;

P represents a pharmacokinetic modifier comprising PEG or PEOX;

m is an integer from 4 to 128 and represents the number of surface pharmacokinetic modifiers.

In some embodiments of the above aspects, L may comprise a PEG of between 2 and 60 monomer units.

In some embodiments of the above aspects, P may comprise a branched or linear PEG of between about 200 and 10,000 Daltons. The total PEG for P may be between about 30 and 85% of the MW of the macromolecule.

In some embodiments of the above aspects, the MW of the macromolecule may be between about 15 kDa and 90 kDa. The MW of the macromolecule may be between about 40 and 90 kDa.

In some embodiments of the above aspects, wherein X is insulin, L may comprise PEG of 12 to 36 monomer units, C comprises lysine, K comprises lysine, n is 14 to 126, P comprises PEG of 4 to 40 monomer units, and m is 16 to 128.

In another aspect, there is provided a macromolecule of Formula I:

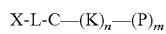   Formula I wherein

X represents a pharmaceutically active agent selected from the group consisting of insulin or an insulin analog;

L represents a linker selected from the group consisting of polyethylene glycol (PEG), polypropylene glycol, polyaryls, peptides, alkyl and alkenyl chains, and saccharides (mono, oligo and poly);

C represents a core moiety having at least three functional groups each separately for attachment to L and attachment to at least two building units K, and wherein C is selected from a diamino or triamino moiety;

K represents a lysine or a lysine analog building unit having at least two branching points for attachment to a pharmacokinetic modifier P or another building unit K;

n is an integer from 14 and 126 and represents the total number of building units, and is a function of the number of generations and the extent of branching of the building units;

P represents a pharmacokinetic modifier comprising PEG or PEOX;

m is an integer from 4 to 128 and represents the number of surface pharmacokinetic modifiers.

It will be appreciated that any one or more of the embodiments as described above for any aspects of the macromolecules may also apply other aspects of the macromolecules.

In another aspect, there is provided a pharmaceutical composition comprising a macromolecule according to any of the above aspects and a pharmaceutically acceptable excipient, carrier or adjuvant.

In some embodiments of the above aspect, the pharmaceutical composition may comprise a concentration of X of at least 5 mg/ml of protein equivalent. The concentration of X may be at least 60 mg/ml of protein equivalent. The concentration of X may be at least 150 mg/ml of protein equivalent. The concentration of X may be at least 250 mg/ml of protein equivalent. The concentration of insulin or insulin analogue may be equal to or greater than about 100 U/ml. The concentration of insulin or insulin analogue may be equal to or greater than about 1000 U/ml. The concentration of insulin or insulin analogue may be equal to or greater than about 4000 U/ml.

In some embodiments of the above aspect, the pharmaceutical composition may have a viscosity below 50 cP.

In some embodiments of the above aspects, the macromolecule is stable at room temperature for greater than 6 months.

In another aspect, there is provided a macromolecule or composition thereof as described herein for use in providing an extended plasma residence time for the pharmaceutically active agent. In another aspect, there is provided a single daily or weekly long acting composition comprising the macromolecule.

In another aspect, there is provided use of the macromolecule as described herein, wherein the pharmaceutically active agent is insulin or an insulin analogue, for the treatment of hyperglycemia, diabetes mellitus, or gestational diabetes. In a further embodiment, the use of the macromolecule is in the manufacture of a medicament for the treatment of hyperglycemia, diabetes mellitus, or gestational diabetes.

In another aspect there is provided a macromolecule or composition as described herein for use in therapy. In a further embodiment, where the pharmaceutically active agent is insulin or an insulin analogue, the macromolecule or composition may be for use in the treatment of hyperglycemia, diabetes mellitus, or gestational diabetes.

In some further embodiments of the above aspects or embodiments, the pharmacokinetic profile of the pharmaceutically active agent X may be improved compared to unconjugated X, by at least 10% increase in AUC. The pharmacokinetic profile of X may be improved compared to unconjugated X, by at least 100% increase in AUC. The pharmacokinetic profile of X may be improved compared to unconjugated X, by at least 200% increase in AUC. The T½ may be 12 to 52 hours. The volume of pharmaceutical composition administered may be less than 1 ml, or less than 500 ul or 250 ul. The pharmaceutically active agent X may be insulin or an insulin analogue, for the treatment of hyperglycemia, diabetes mellitus, or gestational diabetes.

In another aspect, there is provided a method of treatment by administration of the macromolecule or composition thereof to a subject. In an embodiment, there is provided a method of treatment of hyperglycemia, diabetes mellitus, or gestational diabetes, in a subject by administration to the subject of the macromolecule or composition thereof comprising insulin or an insulin analogue.

The above methods or uses may provide an extended plasma residence time in the subject. The extended plasma residence time may provide for a daily or weekly administration regime. It will be appreciated that any one or more of the embodiments as described above for other aspects may also apply to the methods or uses described herein.

BRIEF DESCRIPTION OF THE FIGURES

Embodiments of the present disclosure will now be further described and illustrated, by way of example only, with reference to the accompanying Figures in which.

DETAILED DESCRIPTION

Terms

Figure 1:
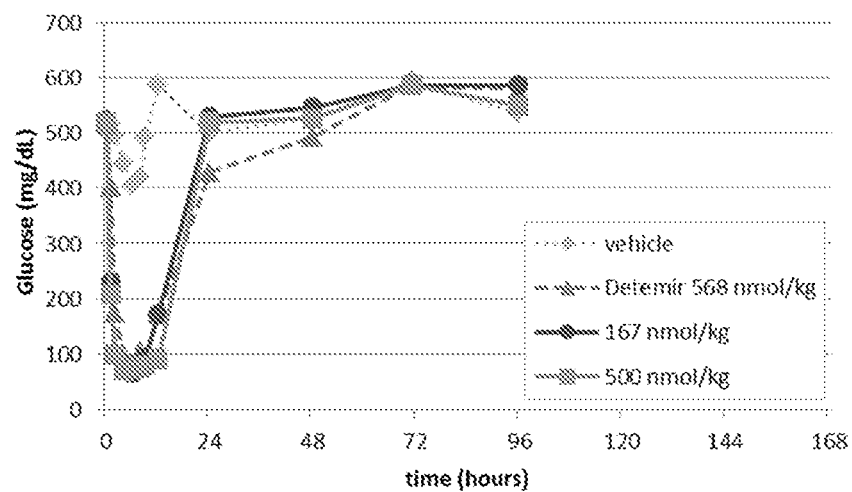
FIG. 1 provides a graph showing glucose (mg/dL) versus time for compound 5.

The term "dendrimer" as used herein refers to a well controlled globular polymeric structure comprising a core from which radiate successive layers of branched monomers (building units), such that the outer layer of monomers provides multiple points of attachment for functional moieties. Dendrimer synthesis can be carefully controlled to ensure a predominantly homogeneous composition.

The term "dendritic motif" as used herein refers to a discrete unit or branch of the macromolecule that can be reacted with a core to form a dendrimer. A dendritic motif includes a building unit covalently joined to at least 2 other building units. Where the building units are lysine or lysine analogues, the apex carboxylate group of the dendritic motif represents the point at which the dendritic motif could be attached to a core or additional building units.

The term "attached" as used herein refers to a connection between chemical components of the macromolecule by way of covalent bonding. The attachment may be direct, or indirect through an intervening moiety or moieties, such as a bridge, spacer, or linker moiety or moieties, which terms may be used interchangeably herein. Furthermore, a linker group or functional moiety or amine may be further modified by a modifier to facilitate the attachment.

The term "selected point of attachment" as used herein refers to a defined point on a dendrimer being uniquely reactable which allows for the controlled placement and attachment of a pharmaceutically active agent. This advantageously allows the position and distribution of a pharmaceutically active agent to be known and controlled.

As used herein, the term "layer" or "generation" refers to a plurality of building units having the same degree of connectivity to the core moiety, i.e. having the same number of building units to connect to the core. For example, building units which are attached to the core moiety are referred to as the first generation. Building units which have one building unit between them and the core moiety are referred to as the second generation. A layer or generation of building units must contain at least two building units.

The term "building unit" used herein refers to a branched molecule having at least three functional groups, one for attachment to the core or a previous generation of building units and at least two functional groups for attachment to the next generation of building units or the surface pharmacokinetic modifier. The building unit may be a subsurface building unit, being part of the layer, or generation, of building units bearing reactive groups that may be further reacted with the reactive group of a further building unit. Each successive layer of building units adds to the valency and size of the dendrimer. The term "surface building unit" as used herein refers to the outermost layer of building units of the macromolecule. i.e. there are no further building units attached to the surface building unit.

The term "surface" as used herein, is used in reference to the outermost layer of building units of the dendrimer.

The term "derivatives" and "fragments" as used herein, and when used in relation to polypeptides, particularly antibodies refers to functional equivalents having similar amino acid sequence, say at least 80, 85, 90, or 95% homology, and retaining, at least to some extent, the activities of the polypeptide.

The term "lysine analogue" as used herein refers to a molecule which has a single apex carboxyl group and two or three primary amine groups. In one instance they may be asymmetric, as for the parent lysine and this is defined as meaning that the bonds and atoms that join the primary amines to the carboxylate apex are different. In a second instance lysine analogues may be symmetrical which is defined to mean that the bonds and atoms that join each primary amine to the carboxylate are identical, and which disregards the asymmetry that is potentially introduced when each primary amine is further reacted.

An "insulin analogue" as used herein refers to a protein having insulin like activity and substantially the same amino acid sequence as human insulin but modified relative to human insulin by one or more natural or non-natural amino acid substitutions, deletions, inversions, or additions. Such compounds are well known in the art. See, e.g., PCT International Patent Application Publication Nos. WO 96/15804 and WO 03/053339; U.S. Pat. Nos. 3,528,960, 5,514,646, 5,618,913, 5,750,497, 6,011,007, 6,251,856; and EP Patent Nos. 254,516 and 280,534. Insulin analogues include insulin aspart, insulin glargine, insulin detemir, insulin degludec and insulin glulisine. Insulin analogues include analogues or insulin modified such as by glycosylation or acylation. The insulin analogue may be a long acting insulin or ultra long acting insulin especially glargine. The pharmaceutically active agent can be insulin with a single amino acid substitution or an insulin with at least one additional amino acids. In certain embodiments the insulin analogue does not include fast acting insulin analogues (duration of action and/or onset less than human insulin), or insulin analogues with Lys (B28) and/or Pro (B29).

The term "insulin activity" as used herein refers to the ability to significantly lower blood glucose levels in at least one generally accepted in vivo Type 1 or Type 2 diabetes animal model. Insulin activity in a long acting insulin composition includes the ability to lower blood glucose to a level of 100 mg/dL or below in a STZ induced diabetic SD rat model for a period of at least 4 hours after a single subcutaneous injection at a dose of 568 nmol/kg insulin or insulin equivalent.

The term "prodrug" is used in its broadest sense and encompasses those derivatives that are converted in vivo, either enzymatically or hydrolytically, to the pharmaceutically active agents.

The term "polyethylene glycol" or "PEG" as used herein refers to a polyalkylene glycol compound or derivative thereof, with or without coupling agents or derivatization with coupling or activating moieties. In its typical form, PEG is a linear polymer with terminal hydroxyl groups and has the formula HO—CH$_2$CH$_2$—(CH$_2$CH$_2$O)n-CH$_2$CH$_2$—OH. The number of repeating subunits "n" in the PEG is approximated for the molecular mass described in Daltons. Typically, PEG reagents used to prepare PEGylated compounds comprise a heterogenous mixture of PEGs having a different number (n) of ethylene glycol subunits in the PEG polymer. A single ethylene glycol subunit (—(CH$_2$CH$_2$O)) of PEG has a molecular weight of about 44 Daltons. Therefore, the molecular weight of the PEG polymer depends on the number (n). PEG may be linear or branched. Branched PEG include trident PEG.

Numerous derivatives of PEG and methods for making them and conjugating them to a protein such as insulin are known in the art and are suitable for use in the present invention. See, e.g., PCT International Patent Application Pub. Nos. WO 01/62827, WO 2006/028745, WO 2006/096535, WO 2006/036825; Zalipsky, S. Bioconjugate Chem. 6:150-165, 1995; Veronese, et al., Applied Biochem. and Biotech. 11:141-152, 1985; and Roberts, M. et al. Advanced Drug Delivery Reviews, 54:459-476, 2002. PEGs as used are typically mixtures of PEG compounds, the molecular weight of a PEG describes the average size of the PEG reagent used.

Three methods are commonly used to calculate MW averages: number average, weight average, and z-average molecular weights. As used herein, the phrase "molecular weight" is intended to refer to the weight-average molecular weight which can be measured using techniques well-known in the art including, but not limited to, NMR, mass spectrometry, matrix-assisted laser desorption ionization time of flight (MALDI-TOF), gel permeation chromatography or other liquid chromatography techniques, light scattering techniques, ultracentrifugation and viscometry.

The ratio of weight average molecular weight and number average molecular weight is known as the polydispersity index (PDI), and provides a rough indication of the breadth of the distribution. PEG reagents are typically polydisperse (i.e., number average molecular weight and weight average molecular weight of the polymers are not equal). The PDI for PEG reagents used to prepare the compounds or compositions of the present invention may be less than about 1.1 or less than about 1.05.

The term "pharmacokinetic profile" refers to the means of representing the fate of a pharmaceutically active agent from the moment it is administered into an animal or person up to the point it is eliminated from the body. At its simplest, a pharmacokinetic profile is represented by the plasma levels of the substance of interest. Pharmacokinetic changes can be measured with metrics such as Cmax, Tmax, T½ (including plasma and effective half life), AUC, peak to trough ratio, T nadir, C nadir, rate of clearance, and volume of distribution. The AUC or T½ may be the pharmacokinetic parameters used to determine improvement. In certain embodiments of the invention, the pharmacokinetic profile is improved by at least 10%, 20%, 30%, 40%, 50%, 60%, 80%, 100%, 150%, or 200% increase in AUC. The pharmacokinetic profile of insulin can be indirectly represented by examining glucose pharmacodynamics. Important factors are the duration and quanta of decrease in plasma glucose; one means of modelling such changes are in STZ rat, dog or pig models. In humans, the change in pharmacokinetic profile of insulin can be evidenced by improved glucose control, for example as measured by Hb1AC or fasting glucose levels.

The term "plasma half-life" or T ½ as used herein means the time following administration at which the plasma concentration of the drug reaches 50% of the maximum concentration of the drug present in the plasma. Plasma half-life is a good indication of effective half-life. "Effective half-life" is the time at which the biological activity of the pharmaceutically active agent is 50% of its initial value. Effective half-life and plasma half-life may be determined by any suitable method known in the art. Duration of blood glucose lowering effect of insulin may be measured by standard methods known in the art. Those of skill in the art appreciate that half-life is a derived parameter that changes as a function of both clearance and volume of distribution. The terms "extended", "longer", or "increased" used in the context of half-life are used interchangeably herein and are intended to mean that there is a statistically significant increase in the half-life of a test compound relative to that of the reference pharmaceutically active agent as determined under comparable conditions.

Macromolecule

The dendrimer may be selected from the group consisting of polyamidoamine dendrimer, polypropylene dendrimer, polyethyleneimine dendrimer, carbohydrate based dendrimer, peptide based dendrimer, polyamino acid dendrimer including polylysine and polyglutamic acid dendrimers, polyester dendrimer, glycopeptide dendrimer, poly aryl amine dendrimer, polyamide dendrimer, poly (alkyl amine) dendrimer, polyamido alcohol dendrimer, cyano dendrimer, polyether dendrimer, polythioether dendrimer, polysiloxane dendrimer, dendritic aryl ester, silicon containing dendrimer, phosphorus containing dendrimer, hydrocarbon dendrimer, or any molecule possessing dendritic framework of controlled architecture. Preferably the dendrimer is biodegradable.

The preparation of lysine and lysine analogue dendrimer polymers is well known and is described by way of example in U.S. Pat. Nos. 4,289,872 and 4,410,688. Well controlled pegylated dendrimers are described in WO2007/048190 and WO2007/082331. Previous studies have suggested that after intravenous administration, uncapped 3H labelled poly-L-lysine macromolecules are rapidly metabolised to free lysine.

A method of preparing pegylated dendrimers is described in WO2008/017215, incorporated herein by reference. In general, the dendrimer has a core which retains a single reactive site that is preserved (by an appropriate protecting group) whilst the remaining sites of the core are utilised for the addition of building units. The protected reactive site of the core is ultimately used to attach a pharmaceutically active agent to the core of the macromolecule.

The macromolecules of the invention may be prepared by a divergent or convergent dendrimer synthesis. Methods for divergent and convergent syntheses are known in the art. In one embodiment, the macromolecule is constructed via a divergent synthesis, wherein the last (surface) layer of building units added may have optionally protected groups and/or bear the pharmacokinetic modifier already attached or are modified with a modifier and/or bear a linker moiety for subsequent attachment of the pharmacokinetic modifier.

Alternatively, in a convergent synthesis, dendritic motifs can be attached to the core or surface groups of a dendrimer. Again, the surface groups of a dendritic motif may be optionally protected and/or may already have pharmacokinetic modifiers attached, and/or are modified with a modifier and/or bear a linker moiety for the pharmacokinetic modifier.

The macromolecules of the invention are typically purified using one or more purification techniques such as ion exchange chromatography, size exclusion chromatography, affinity chromatography, hydrophobic interaction chromatography, and/or reversed-phase chromatography. The overall heterogeneity of the compounds (number and proportion of PEGylated insulin compounds generated from a PEGylation reaction) in a sample can be assessed using one or more of the following methods: chromatography, electrophoresis, mass spectrometry, and in particular, MALDI-MS, and NMR spectroscopy.

Exemplary macromolecules contemplated herein may be conveniently represented according to the following Formula I:

X-L-C—[K]$_n$—[P]$_m$

Embodiments of the above Formula I are described as follows.

X represents a pharmaceutically active agent. In one embodiment, X is a protein or peptide. X can be selected from the group consisting of insulin, an insulin analogue, GLP-1 and GLP-1 analogue. In a particular embodiment, X is insulin or an insulin analogue. It will be appreciated that the pharmaceutically active agent has, or can be modified to have a functional group for attachment to the linker group L.

L represents a linker. It will be appreciated that L can provide a linear spacer group between the core of the dendrimer and the pharmaceutically active agent. The linker group L may include functional groups for attachment to the pharmaceutically active group and core of the dendrimer. In one embodiment, L comprises a PEG group. The PEG group may be linear and between 2 and 48 units (i.e. [PEG]$_{2-48}$). In a further embodiment, the PEG is between 9 and 36 units, or between 12 and 24 units. In a further embodiment, the PEG is 12, 16, 18, 20, 24, or 36 units. The linker may comprise of a single PEG group, or the linker may comprise smaller PEG groups joined together via reactive functionalities, for example -[PEG]$_{1-20}$-Y-[PEG]$_{1-20}$- where Y is an intervening functional group.

C represents a core moiety having at least three functional groups each separately for attachment to L and at least two building units K. C may be a have three reactive nitrogens, for example a triamino compound, such as a diC$_{1-10}$alkylene triamine, for example dipropylene triamine.

K represents a building unit, such as a lysine or a lysine analog, having at least two branching points for attachment to a pharmacokinetic modifier P.

n represents the total number of branched building units (including surface and subsurface building units), and is a function of the number of generations and the extent of branching of the building units. n may be an integer between 14 and 126. By way of example, where each generation comprises building units having 2 amino groups, m is an integer between 14 and 126, for example 14, 30, 62 or 126, and n is about 30 or 62. By way of example, where each generation comprises building units having 2 amino groups, n is an integer between 14 and 126, then m is between 16 and 128, for example n is 14, 30, 62 or 126, and m is about 16, 32, 64 or 128, respectively.

P represents a pharmacokinetic modifier, such as a PEG, for example methoxy-PEG. In one embodiment, the surface PEG is between about 30 and 85% of the MW of the macromolecule, between 50 and 85%, or between 60% and 85%. In a further embodiment, the surface PEGs are between 4 and 24 ethylene units in length. The PEGs may comprise 8, 12, 16, 20, 24 or 48 ethylene units. Trident PEGs may be used. In another embodiment, the trident PEG comprises (methyl-PEG$_{12}$)$_3$-PEG$_4$ (e.g. prepared after coupling on thermo scientific #22424), (methyl-PEG$_8$)$_3$-PEG$_4$ or (methyl-PEG$_4$)$_3$-PEG$_4$.

m represents the number of pharmacokinetic modifiers attached to the surface building units and is a function of n. By way of example, where the surface building units having 2 functional groups for attachment to the pharmacokinetic modifier or next generation, then m=n+2. m may be an integer from 4 to 128 (for example 8, 16, 32, 64 or 128). In one embodiment, m is an integer between 32 and 64.

By way of further example, using a triamino core, and lysine as the building unit, the following generations are correlated to numbers of building units and PK modifiers:

| Number of Generations | Building units (n) | Surface building units | PK modifiers on surface (m) |
| --- | --- | --- | --- |
| 3 | 14 | 8 | 16 |
| 4 | 30 | 16 | 32 |
| 5 | 62 | 32 | 64 |
| 6 | 126 | 64 | 128 |

In one embodiment, the dendrimer is from 3 to 6 generations (G3 to G6). In a further embodiment, the dendrimer is 4 (G4) or 5 (G5) generations. In a particular embodiment, the dendrimer has 5 generations (G5).

In certain embodiments, the macromolecule has a MW greater than about 16 kDa, and can be greater than about 20, 25, 30, 35, 40, 45, 50, 55, 60, 65, 70, 75, 80 kDa. In another embodiment, the MW is less than about 120 kDa, 100 kDa, 80 kDa, 60 kDa. The MW of the macromolecule may be between about 15 kDa and 90 kDa, 23 and 86 kDa or 40 kDa and 86 kDa.

Figure 9:
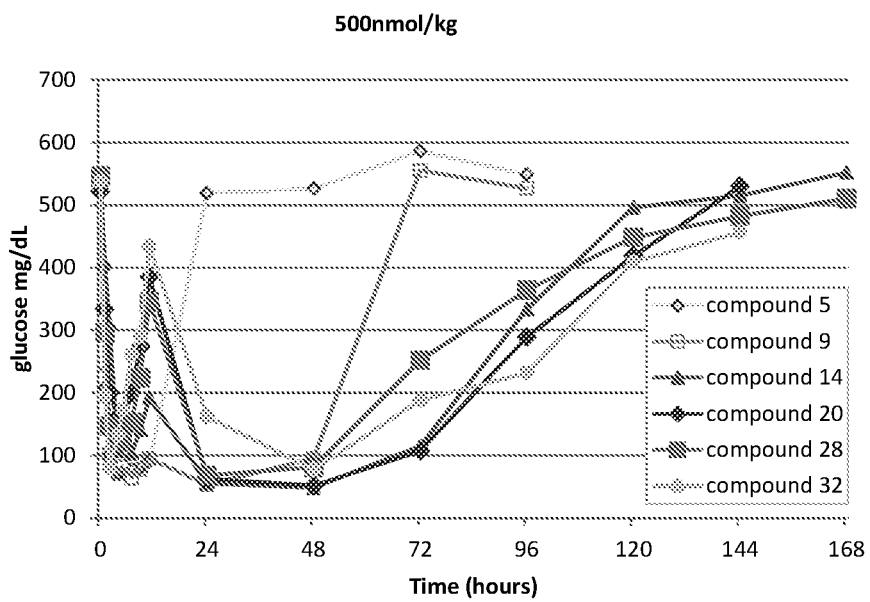
FIG. 9 provides a graph showing comparison of mean serum glucose levels for compounds 5, 9, 14, 20, 28, and 32.

As shown in FIG. 9, the larger macromolecules have similar pharmacodynamic profiles, but elicit differing responses in the 12 to 24 hours subsequent to administration. In another embodiment the macromolecule is between about 30 and 60 kDa or 35 kDa to 55 kDa, to provide better short and long term glucose control.

Building Units

Suitable building units include amino acids such as glutamic acid, polyester branching units, lysine, and analogues thereof. In one embodiment, the macromolecules as described herein are constructed from at least one layer of lysine or lysine analogue building units. As used herein, the term "lysine analogue" refers to a moiety having a carboxy group that reacts with an amino group of the core or an earlier generation of building units and at least two amino groups that react with the carboxy group of a subsequent generation of building units or form the surface amino groups of the dendrimer. Examples of lysine and lysine analogue building units contemplated by the invention include the following (where # depicts the carbonyl residue of the apex carboxyl group for attachment to the core or preceding building unit):

Lysine* 1 having the structure:

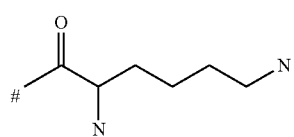

Analogue 2, having the structure below, where a is an integer 0, 1 or 2; and b and c are independently integers 2, 3, 4, 5 or 6:

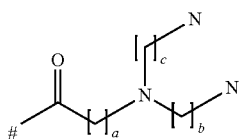

2

Analogue 3, having the structure below, where a is an integer 0, 1, 2, 3, 4 or 5; and b and c are independently integers 1, 2, 3, 4 or 5, and in a further embodiment a is an integer 0, 1 or 2:

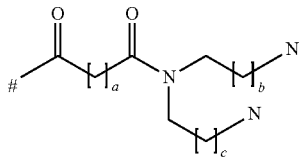

3

Furthermore, any methylene group of the building units may be replaced by a methyleneoxy (CH$_2$—O) or ethyleneoxy (CH$_2$—CH$_2$—O) group, provided that this does not result in the formation of a carbonate (—O—C(O)—O—) or carbamate (—O—C(O)—N—) moiety within the building unit.

Core

The building units are reacted with a core compound. A core may be any compound containing three or more reactive groups, one is the selected point of attachment for the pharmaceutically active agent, either directly or indirectly through a linker, and the other two or more reactive groups are the points of attachment for the building units or dendritic motif, either directly or indirectly. The selected point of attachment reactive group is typically orthogonal to the other 2 or more reactive groups. Suitable reactive groups include hydroxyl, carboxy, active esters such as NHS ester, PyBOP, PFP esters, amino, azide, maleimides including citraconyl, SMCC, alkynes including BCN, DBCO, thiol, protected thiol, carbonyl groups such as aldehydes and ketones, alkoxyamines, haloacetate, biotin, tetrazines, transcyclooctenes, and PTAD tyrosine reactive groups.

In certain embodiments, the core has 2 or more reactive nitrogens. In one particular embodiment, the core has three reactive nitrogen atoms. Examples of cores contemplated by the invention include the following (where # depicts the selected point of attachment for the pharmaceutically active agent):

Core 4 having the structure below where a and b are independently integers 1, 2, 3, 4 or 5, such as 2 or 3, and in a further embodiment a and b may be the same:

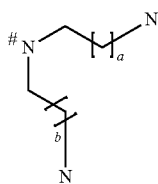

4

A hetero-bifunctional core can be prepared by reacting one nitrogen atom of a triamino compound with a suitably functionalised carboxy spacer to form a core compound that has one selected point of attachment reactive group and two amino groups for attachment of the building units. An example is Core 5 having the structure below:

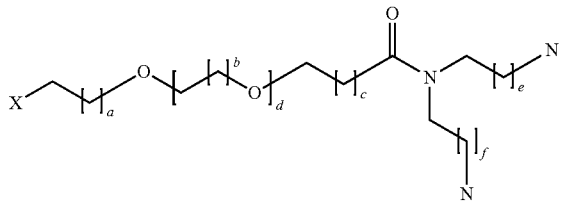

5 where x is the selected point of attachment reactive group selected from hydroxyl, carboxy, active esters such as NHS ester, PyBOP, PFP esters, amino, azide, maleimides including citraconyl, SMCC, alkynes including BCN, DBCO, thiol, protected thiol, carbonyl groups such as aldehydes and ketones, alkoxyamines, haloacetate, biotin, tetrazines, transcyclooctenes, or PTAD tyrosine reactive groups, and a, b, c, e and f are independently integers 1 to 5, such as 1, 2 or 3; and d is an integer from 0-100, such as 1-30. In one embodiment, d is an integer of 1-5, 6-10, 11-15, 16-20, 21-25 or 26-30. In another embodiment, x is a carboxy, thiol, maleimide or azide. In a particular embodiment, x is an alkyne, for example DBCO or BCN. In another embodiment, a is 1 to 3, b, e and f are independently 1 or 2, c is 1 to 3, d is 2 to 48. In a particular embodiment, a, b, and c are 1, e and f are 1 or 2, d is 12 or 24.

The core may be prepared by reacting a suitably functionalised amino spacer with lysine or a lysine analogue to form a core compound that has one reactive group that ultimately becomes the point of attachment for the pharmaceutically active agent while the at least two amino groups become the points of attachment for the building units. Examples are Cores 6 and 7 having the structures below:

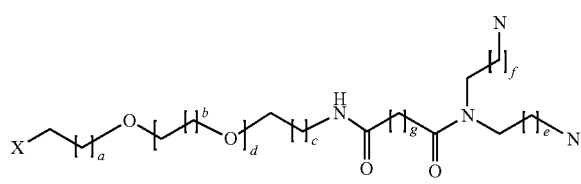

6

7

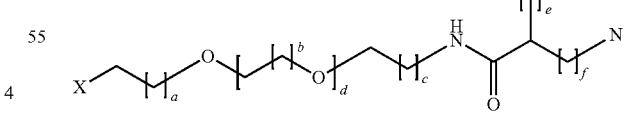

where x is the selected point of attachment reactive group selected from hydroxyl carboxy, active esters such as NHS ester, PyBOP, PFP esters, amino, azide, maleimides including citraconyl, SMCC, alkynes including BCN, DBCO, thiol, protected thiol, carbonyl groups such as aldehydes and ketones, alkoxyamines, haloacetate, biotin, tetrazines, transcyclooctenes, or PTAD tyrosine reactive groups, and a, b, c, e, f and g are independently integers 0 to 5, such as 1, 2 or 3; and d is an integer from 0-100, such as 1-30. In one embodiment, d is an integer of 1-5, 6-10, 11-15, 16-20, 21-25 or 26-30.

In another embodiment, x is a carboxy, thiol, maleimide or azide. In a particular embodiment, x is an alkyne, for example DBCO or BCN. In another embodiment a, b, c and g are independently 1 to 4; e and f are independently 0 to 4 and d is 2 to 48. In a particular embodiment a, b, c are 1 or 2; e is 0 to 4; f and g are independently 2 to 4 and d is 12 to 24.

In a particular embodiment of Core 6, each of a, b, c and d are 1 (NEOEOEN) where each of e, f and g are 2. In a further particular embodiment of Core 6, each of a, b, c are 1 d is 12 or 24, e and f are 1 or 2, g is 2. In a particular embodiment of Core 7, each of a, b, c are 1 d is 12 or 24, e is 0, f is 4.

Pharmaceutically Active Agent

As used herein, a pharmaceutically active agent includes any molecule or precursor thereof, or residue thereof, which is capable of imparting a physiological effect or reaction after administration to a subject, either alone or in conjunction with another pharmaceutically active agent. The term also encompasses agents or residues thereof which in themselves may not impart a physiological effect or the desired level thereof, but in conjunction with one or more other pharmaceutical agents, or when attached to the dendrimer, provides the desired physiological activity. Pharmaceutically active agents contemplated herein may be naturally occurring, including modifications and derivatives of naturally occurring molecules, or may be synthetic and examples contemplated herein include, polymers, (non-dendritic and dendritic, where the dendritic moiety can have the same number of generations or a different number of generations to the macromolecule), saccharides, oligosaccharides, polysaccharides, amino acids, peptides, oligopeptides, polypeptides, proteins, glycoproteins, nucleic acids and nucleotides. Particular pharmaceutically active agents contemplated are intended for therapeutic or prophylactic applications. Examples of physiological effects or reactivity imparted by pharmaceutically active agents include depressing or stimulating biological reactions, for example through binding to a substrate, replacement or addition of substances, removal of deleterious substances and cellular death.

It will be understood that the pharmaceutically active agents, may be present as pharmaceutically acceptable salts or prodrugs.

Protein-based drugs have been developed that provide significant clinical benefit to the patient, but in many cases these drugs require frequent dosing and large dose sizes. This is because the physio-chemical properties of the protein drugs lead to their rapid renal excretion or metabolic clearance. Advantageously, when attached to a dendrimer as described herein, the pharmacokinetic properties of the protein may be beneficially altered.

Thus, in certain examples of the invention, the pharmaceutically active agent(s) of the macromolecule may be amino acid based such as a protein, a glycoprotein, a peptide, oligopeptide, polypeptide or an enzyme or derivatives thereof. The term polypeptide, protein or peptide means at least 5 amino acids connected by peptide bonds. Amino acids may be natural or non-natural amino acids.

Examples of proteins and peptides include insulin, insulin analogs or mimetics, insulin precursors, glucagon, GLP-1, GLP-2, IGF-I, IGF-II, TGF α or β, GRF (growth hormone releasing factor), protein C, a blood coagulation factor, heparin, exendin-3, exentidin-4, or a functional analogue of any thereof.

Other proteins and peptides include haemoglobin, serum proteins such as blood factors including Factors VII, FII, FV, FVII, FVIII, FIX FX, FXI, FXII, and FXIII or an analogue of any thereof, protein C, protein S, tPA, PAI-1, tissue factor, as well as sequence, variants thereof; antibodies and fragments and mimetics thereof, cytokines, colony stimulating factors and phospholipase-activating protein (PUP), plant proteins such as lectins and ricins, tumor necrosis factors and related alleles, receptors such as TNF and IL receptors, growth factors, hormones, somatomedins, EPO, hypothalamic releasing factors, TPA, aprotinin, tissue factor pathway inhibitor or other protease inhibitors, Anti-inflammatory selected from the group consisting of cyclooxygenase inhibitors, non-steroidal antiinflammatory drugs (NSAIDs), antigout drugs, anti-rheumatoid drugs, 5-lipooxygenase inhibitors, cysteinyl leukotriene receptor antagonist, cytokines inhibitors, phosphodiesterase inhibitors, H1 receptor antagonist, immunomodulators, immunosuppressive agents.

The enzymes may be selected from carbohydrate specific enzymes, proteolytic enzymes, oxidoreductases, transferases, hydrolases, lyases, isomerases and ligases. Examples of enzymes include asparaginase, arginase, arginine deaminase, adenosine deaminase, superoxide dismutase, endotoxinases, catalases, chymotrypsin, lipases, uricases, adenosine diphosphatase, tyrosinases, and bilirubin oxidase. Carbohydrate-specific enzymes of interest include glucose oxidases, glycosidases, glucocerebrosidases, glucuronidases, etc.

Peptides and proteins that do not contain glycan moieties may be glycosylated either enzymatically using glycosyltransferases, or chemically synthesised, for example by using standard peptide chemistry and glycosylated amino acid components such as N-galactosylated asparagine. Alternatively glycosylation sites may be engineered into proteins or peptides which in vivo normally are produced in their non-glycosylated form.

The pharmaceutically active agent of the macromolecule may alternatively, or in addition, include a water-insoluble pharmaceutical, a water-soluble pharmaceutical, a lipophilic pharmaceutical, or mixtures thereof.

The pharmaceutically active agent may be exemplified by, but not limited to one or more types selected from the groups in Table 1.

TABLE 1

| Pharmaceutically active agents | |
| --- | --- |
| Antibodies | Anti-arthritic agents |
| Anti-fungals | Anti-histamines |
| Anti-infectives | Anti-inflammatories |
| Anti-protozoals | Anti-microbials |
| Antiviral pharmaceuticals | Anti-parasitic agents |
| Biologicals | Behaviour modification drugs |
| Bronchodilators and expectorants | Blood factors |
| Cardiovascular pharmaceuticals | Cancer therapy and related pharmaceuticals |
| Contraceptives | Central nervous system pharmaceuticals |
| Diabetes therapies | Fertility pharmaceuticals |
| Growth hormones | Growth promoters |
| Hematinics | Hemostatics |
| Hormone replacement therapies | Hormones and analogs |
| Immune suppressives | Immunostimulants |
| Muscle relaxants | Natural products |
| Obesity therapeutics | Osteoporosis drugs |
| Ophthalmic pharmaceuticals | Peptides and polypeptides |
| Pain therapeutics | Respiratory pharmaceuticals |
| Proteins | Transplantation products |

The present invention is particularly appropriate for pharmaceuticals that are very active even in extremely small quantities or whose sustained long-term administration is sought.

Pharmacokinetic Modifier

A pharmacokinetic modifying agent includes any molecule or residue thereof which can modify or modulate the pharmacokinetic profile of a pharmaceutically active agent or the dendrimer bearing the pharmaceutically active agent, including that of absorption, distribution, metabolism and/or excretion. In a particular embodiment, the pharmacokinetic modifying agent is selected to prolong the plasma half-life of the pharmaceutically active agent or macromolecule.

The pharmacokinetic modifying agent may include polyfluorohydrocarbons, fatty acids, lipids, oligo- and polysaccharides such as hesylation, deoxycholic acids (bile acids), polyhydroxylated compounds such as N-(2-hydroxypropyl)methylacrylamide polymers (HPMA) and RAFT polymers, poly(glutamic acid) and polylactide type structures, or a polyethylene glycol (PEG), or polypropyleneglycol, and alkyl capped forms thereof, or polyethyloxazoline (e.g. PEOX) motif.

In a particular embodiment, a PEG for use in the invention is a PEG having one end of the polymer terminating with a relatively inert group, such as a lower $C_{1-6}$alkoxy group. In one embodiment, the PEG is a monomethoxy-PEG (commonly referred to as mPEG), wherein one terminus of the polymer is a methoxy (—$OCH_3$) group. In a further embodiment, the PEG used in the invention is an "activated mPEG" in which one end of the linear PEG terminates with a methoxy group and the other end terminates with a reactive group appropriate for coupling to the surface building units of the dendrimer.

The PEG groups may include relatively short ethylene glycol chains, for example PEG groups including one or more of the following:

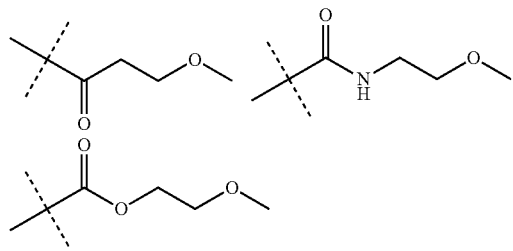

Trident PEGs may be used. In one embodiment, the trident PEGs comprise (methyl-$PEG_{12}$)$_3$-$PEG_4$ (prepared after coupling on thermo scientific #22424), (methyl-$PEG_8$)$_3$-$PEG_4$ or (methyl-$PEG_4$)$_3$-$PEG_4$.

In another embodiment, the ratios of pharmacokinetic modifier to pharmaceutically active agent is in the range of 128:1 to 2:1, such as 64:1 to 4:1, and particularly 32:1 to 16:1. In another embodiment, the surface PEG is between 30 and 85% of the total MW of the macromolecule.

In an embodiment, the PEG chains are relatively monodisperse and chosen from a molecular weight range between 200 and 10,000 Daltons. In a particular embodiment, the PEG chains are chosen from a molecular weight range between 200 and 5000 Daltons, 200 and 2500 Dalton 1000 and 2500 daltons or 200 and 850 daltons. In a further embodiment, the PEG is 1100 or 2000 daltons MW. In another embodiment, the PEG are between 4 and 24 ethylene units in length. In a further embodiment, the PEG chains comprise 8, 12, 16, 20, 24 or 40 ethylene units.

The pegylated macromolecules according to embodiments as described herein may improve physiochemical properties of the pharmaceutically active agent by providing chemical stability, as well as improving the solubility of pharmaceutically active agents; increase the circulating lifespan of the macromolecule in the plasma by reducing glomerular filtration and reducing the access of macromolecule to certain tissues or organs; reduce the immunogenicity and toxicity of pharmaceutically active agents; and/or shield against metabolism by reducing proteolytic attack by enzymes.

The macromolecules as described herein can provide a shielding effect whilst not entrapping or entangling the pharmaceutically active agent and thereby maintaining its efficacy.

In certain embodiments, the use of multiple low MW surface PEG chains attached to a biodegradable dendrimer can break down into benign components and be safely eliminated in vivo.

Further the low MW PEG chains utilised in this invention can provide high solubility without an increase in viscosity commonly associated with PEGylation. Low MW PEG is smaller than about 5000 kDa.

In certain embodiments, the macromolecules as described herein are prepared by covalently attaching an activated PEG to the surface of a dendrimer or dendritic motif. The reaction conditions for conjugation to the dendrimer will vary depending upon the particular dendrimer and linking chemistry employed, the particular type of reactive group on the surface of the dendrimer, and the like, and can readily be determined by one skilled in the art. Optimized experimental conditions for a particular PEGylation strategy can readily be determined, typically by routine experimentation, by one skilled in the art.

Linkers

As described above, the pharmaceutically active agent may be attached to the macromolecule at a selected site of attachment either directly or via a cleavable or non-cleavable linker. Cleavable linkers may be designed to be enzymatically cleaved, and may for example, be used in macromolecules targeted to tissues expressing those enzymes. Alternatively, an acid labile linker may be preferred such that the compound attached to it is released under acid conditions, such as in hypoxic tissue. Cleavable linkers release the pharmaceutically active agent from the dendrimer in order to effect biological or pharmaceutical action. Non-cleavable linkers are linkers that do not need to release the pharmaceutically active agent from the dendrimers to achieve effective biological or pharmaceutical action.

The term "linker" refers herein to any chemical entity which serves to link the pharmaceutically active agent to the dendrimer core. Exemplary linkers contemplated by the present invention include polymers such as polyethylene glycol (PEG), polypropylene glycol, polyaryls, peptides, alkyl and alkenyl chains, and saccharides (mono, oligo and poly).

In particular embodiments, the linker comprises a PEG chain, such as from 2-60 ethyleneoxy repeat units, for example from 2-20 or 20-48 repeat units. In one embodiment, the PEG is from 8 to 36 repeat units. In a further embodiment, the PEG is 12, 16, 20, 24 or 36 repeat units. Especially with dendrimers that are sterically crowded, linkers may be of a suitable length that the pharmaceutically active agent can protrude beyond the surface pharmacokinetic modifiers extending from surface of the dendrimer, to allow for in vivo binding of the agent to its receptor or similar.

For the attachment of the linker to the pharmaceutically active agent and/or the dendrimer core, the linker can comprise one or more reactive functional groups. In particular embodiments, the reactive functional groups comprise of groups such as hydroxy, carboxy, active esters such as NHS ester, PyBOP, PFP esters, amino, azide, maleimides including citraconyl, SMCC, alkynes including BCN, DBCO, thiol, protected thiol, carbonyl groups such as aldehydes and ketones, alkoxyamines, haloacetate, biotin, tetrazines, trans-cyclooctenes and PTAD or other tyrosine reactive groups.

In particular embodiments, the linker consists of a PEG chain with a reactive carboxyl group for joining to an amine at the core of the dendrimer and an azide group for conjugating to a pharmaceutically active agent containing a reactive alkyne moiety.

In particular embodiments, the linker consists of a PEG chain with a reactive amine group for joining to a carboxyl group at the core of the dendrimer and an azide group for conjugating to a pharmaceutically active agent containing a reactive alkyne moiety.

In particular embodiments, the linker consists of a PEG chain with a reactive carboxyl group for joining to an amine at the core of the dendrimer and an alkyne group for conjugating to a pharmaceutically active agent containing a reactive azide moiety.

In particular embodiments, the linker consists of a PEG chain with a reactive carboxyl group for joining to an amine at the core of the dendrimer and a maleimide group for conjugating to a pharmaceutically active agent containing a reactive thiol moiety.

In particular embodiments, the linker consists of a PEG chain with a reactive amine group for joining to a carboxyl group at the core of the dendrimer and a thiol or masked thiol group for conjugating to a pharmaceutically active agent containing a reactive maleimide moiety.

Conjugation sites on the pharmaceutically active agent of proteins can be cysteine, lysine, N-terminal amines, tyrosine, carbohydrates, non-natural amino acids or transaminase or recognition sequences. Binding sites for conjugating to proteins are known in the art, (for example, Milla P., et al, Current Drug Metabolism (2012) V13, 1:105-119.) In one embodiment, the core is attached either directly or indirectly via a linker to the epsilon-amino group of the lysine at position 29 of the B-chain or equivalent position in an insulin analog, eg position 27, 28 or 30 in an insulin with addition, deletion or amino acid substitution to add lysine. In a particular embodiment, the conjugation is at position 29 of the B chain of insulin.

Conjugation of a non-cleavable linker to a pharmaceutically active agent must not impede the active site of the protein or peptide. The conjugation site is may be distal from the site of activity to avoid reducing efficacy.

Selection of the linker conjugation site and chemistry can provide a substantially homogeneous composition of macromolecules. In one embodiment, the linker conjugation to the pharmaceutically active agent provides a composition of at least 50%, at least 60%, at least 80% or at least 90% of a single species of macromolecule.

A linker may be used in a number of ways to attach a pharmaceutically active agent to the core. In a first method, the linker may be attached to the core of the dendrimer and the pharmaceutically active agent is attached to the linker via reactive functional groups. Alternatively, the linker may be first attached to the pharmaceutically active agent and then attached to the core of the dendrimer via reactive functional groups. In a third method, both the core and the pharmaceutically active agent can be attached to a linker or linker component and the two linker moieties subsequently reacted together via reactive functional groups to provide the linker moiety between the core and the pharmaceutically active agent. Conjugation methods well known and are described in Bioconjugate Techniques, Greg T. Hermanson (Academic Press) 2013.

In an embodiment, a macromolecule of Formula I may be provided by a macromolecule of Formula II:

Formula II

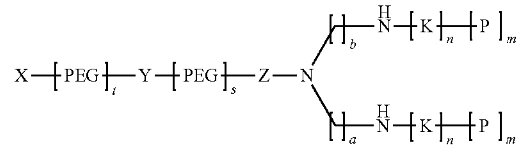

In the above Formula II, each of X, K, P, n and m, may be defined according to any of the previous embodiments described above for these terms. a and b may be each independently an integer of 1 to 5. In another embodiment, a and b are the same. In a further embodiment, a and b are each 3.

In the above Formula II, -[PEG]$_t$-Y-[PEG]$_s$-Z is a linker group for attachment of the pharmaceutically active agent X to the core of the dendrimer. t may be an integer from 0 to 30. s may be an integer of 8 to 36. In an embodiment, t is 0. In an embodiment, s and t are integers independently selected from 12, 16, 20, 24 or 36. Y and Z can comprise one or more reactive functional groups selected from hydroxy, carboxy, active esters such as NHS ester, PyBOP, PFP esters, amino, azide, maleimides including citraconyl, SMCC, alkynes including BCN, DBCO, thiol, protected thiol, carbonyl groups such as aldehydes and ketones, alkoxyamines, haloacetate, biotin, tetrazines, trans-cyclooctenes and PTAD or other tyrosine reactive groups. In a particular embodiment, Z is a reactive carboxyl group. In another embodiment, Y is an azide group or maleimide group or alkyne group such as BCN or DBCO.

Composition

The invention further provides for the use of macromolecules as described herein in therapy.

Subjects to be treated include mammalian subjects: humans, primates, livestock animals (including cows, horses, sheep, pigs and goats), companion animals (including dogs, cats, rabbits, guinea pigs), and captive wild animals.

In certain embodiments, the macromolecules according to the invention, when administered according to the desired dosing regimen, at least partially attain a desired therapeutic or prophylactic effect, including one or more of: alleviating the symptoms of, preventing or delaying the onset of, inhibiting the progression of, or halting or reversing altogether the onset or progression of the particular disorder or condition being treated.

In another aspect the invention also contemplates compositions comprising a macromolecule as described herein together with a pharmaceutically acceptable excipient, carrier or adjuvant thereof. The formulation of such compositions is well known to those skilled in the art, see for example, *Remington's Pharmaceutical Sciences,* 18$^{th}$ Edition, Mack Publishing, 1990. The composition may contain any suitable carriers, diluents or excipients. These include all conventional solvents, dispersion media, fillers, solid carriers, coatings, antifungal and antibacterial agents, surfactants, isotonic and absorption agents and the like.

The carrier must be pharmaceutically acceptable in the sense of being compatible with the other ingredients of the composition and not injurious to the subject. Compositions include those suitable for oral, nasal, topical (including dermal, buccal and sublingual), or parental (including subcutaneous, intramuscular, intravenous and intradermal) administration. In general, the compositions are prepared by uniformly and intimately bringing into association the active ingredient with liquid carriers or finely divided solid carriers or both. In one embodiment, the composition has a pH of 7-7.5.

Compositions of the present invention suitable for administration may be presented as single or multi-use vials containing a predetermined amount of the active ingredient; as a solution or a suspension in an aqueous or non-aqueous liquid.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents.

Suitable pharmaceutically acceptable salts include, but are not limited to salts of pharmaceutically acceptable inorganic acids and base salts.

In certain further embodiments, the compositions comprise compounds of Formula I wherein greater than about 80%, or greater than 90% of the macromolecules in the composition are homogeneous.

Pharmaceutical compositions of this invention can be administered to mammals including humans in a manner similar to other therapeutic agents in treatment-effective amounts. A treatment effective amount is intended to include an amount which, when administered according to the desired dosing regimen, at least partially attains the desired therapeutic or prophylactic effect, as above. The dosage to be administered, and the mode of administration, will depend on a variety of factors including age, weight, sex, condition of the patient and genetic factors, and will ultimately be decided by medical personnel subsequent to experimental determinations of varying dosage followed by imaging as described herein. In general, dosage required for therapeutic efficacy will range from about 0.001 to 50,000 µg/kg, or between 0.01 to 25.0 µg/kg of host body mass. The optimal dose will be determined empirically following the disclosure herein.

Identification of optimal basal insulin dose is based in part on trial and error, and in part on protocols that have developed from best practice. However, optimal dosing will generally need to be individualised, and depends of the severity of the condition. Some patients metabolise insulin more quickly than others, and have differing levels of insulin resistance. In addition dosing regimens will depend upon the effective half-life of the macromolecule. In some embodiments the composition of the present invention is delivered at an interval 3-5 times the effective half-life to maintain steady state kinetics.

In clinical practice, it takes 3 to 5 times the half-life for a drug's serum concentration to reach steady state after regular dosing is started, stopped, or the dose changed. The macromolecule may be administered on average every day, every 2nd day, every 3rd day, every 4th day, every 5th day, every 6th day or every week, or every fortnight. In one embodiment, the macromolecule is administered less frequently than daily, less frequently than every second day, less frequently than every third day, less frequently than every 6 days. In certain embodiments, the time of dose is flexible and the patient is not required to administer the dose at the same hour of day. In another embodiment, the dose can be delivered in a 2 hour, 3 hour, 4 hour, 5 or 6 hour window.

The half-life of the macromolecule can be suitable for a daily, weekly or biweekly administration. Half-life improvement can be by at least 10%, 20%, 30%, 40%, 50%, 60%, 80%, 100%, 150%, or 200%. Improvement may be in plasma, effective or terminal half-life. In vivo activity may be detectable for greater than 12 hours, or in further embodiments greater than 24 hours, 48 hours, 72 hours, 96 hours, 120 hours, 144 hours or 168 hours. The macromolecule can reduce blood glucose below 400, 300, 200, 100 mg/dL for greater than 24 hours, 48 h, 72 h, 96 h, or 120 h when measured in the fasting state. In some embodiments, the macromolecule can reduce blood glucose below 300 mg/dL for greater than 24 hours, when measured in a fasting state. In some embodiments half-life is improved such that insulin activity includes the ability to lower blood glucose to a level of 100 mg/dL or below in a STZ induced diabetic SD rat model for a period of at least 4 hours after a single subcutaneous injection at a dose of 568 nmol/kg insulin or insulin equivalent, optionally detemir.

In some embodiments the macromolecules of the present invention reduce incidence of hypoglycaemia in a patient or patient population. In an embodiment, the incidence of hypoglycaemia is reduced by at least 10%, 20%, 25%, 30% or 50%. In some embodiments the reduction is hypoglycaemia is determined by comparison to use of daily long acting insulin glargine or degludec or detemir.

In some embodiments the macromolecules of the present invention reduce incidence of hyperglycaemia in a patient or patient population. In an embodiment the incidence of hyperglycaemia is reduced by at least 10%, 20%, 25%, 30% or 50%. In some embodiments the reduction is hyperglycaemia is determined by comparison to use of daily long acting insulin glargine or degludec or detemir.

For type 1 diabetics, total daily insulin should be approximately 0.5-1.0 unit/kg/day and 40-50% of total daily insulin should be basal insulin. For newly diagnosed type 1 diabetes the initial total daily insulin should be estimated based on the level of ketones, but should generally range from 0.5 to 0.7 mg/kg (or for existing diabetics, the level of HA1C). Doses should be titrated to achieve fasting blood glucose of 4.0-5.0 mmol/L.

In type 2 diabetics, the starting dose will be related to the level of HA1C. The goal is to achieve HbA1c in the range of about 7-9% and/or fasting glucose of 3.9 to less than 6.0 mmol/L. Insulin may be started at 6 units and be increased by 2-4 units every week until daily monitoring shows that the target fasting glucose levels are achieved on most mornings. The total daily insulin requirement is generally about 40-60 units but is higher in those with obesity, higher initial concentrations of HbA1c, and elevated hepatic enzymes which are surrogate measures of fatty liver and insulin resistance.

Pharmaceutical compositions of this invention can be administered in a concentrated form. The compositions may be administered in a concentration of at least 5, 10, 20, 40, 60, 80, 100, 150, 200, or 250 mg/ml of protein equivalent. In an embodiment, the concentration of insulin or insulin analog is equal to or greater than about 100 U/ml, 200 U/ml, 400 U/ml, 600 U/ml, 800 U/ml, 1000 U/ml, 1200 U/ml, 1400 U/ml, 1600 U/ml, 1800 U/ml, 2000 U/ml, 3000 U/ml or 4000 U/ml where 1 U=28.8 ug insulin equivalents. Insulin dendrimers of the present invention were made and solubilised at as shown in example H. The viscosity of the formulation may be below 50 cP.

In certain embodiments the higher macromolecule concentration enables the volume of pharmaceutical composition administered to be lower than the pharmaceutically active agent alone. Lower volumes are preferred by patients for comfort and ease of administration. The volume of pharmaceutical composition administered may be less than 1 ml, or less than 500 ul or 250 ul.

Pharmaceutical compositions of this invention can be administered to patients in amounts that do not cause substantial weight gain. In an embodiment, the compositions result in less than less than 4%, or less than 2% weight gain in the first month of administration.

In certain embodiments, the pharmaceutical composition does not result in PEG related toxicity or bioaccumulation. In some embodiments the presence of PEG is not detectable in the kidneys or choroid plexus of patients administered with the macromolecule for chronic conditions which require long term treatment, such as diabetes, or hormone replacement.

It will be understood that the invention disclosed and defined in this specification extends to all alternative combinations of two or more of the individual features mentioned or evident from the text or drawings. All of these different combinations constitute various alternative aspects of the invention.

The present invention will now be more fully described with reference to the accompanying examples. It should be understood, however, that the description following is illustrative only and should not be taken in any way as a restriction on the generality of the invention described above.

EXAMPLES

The invention will now be described with reference to the following non-limiting illustrative examples and figures.

A system of nomenclature has been developed for the purposes of identifying the individual compounds described in this patent. This nomenclature is used to simplify the description of the compounds and is used in place of what would be a complex IUPAC name, the use of which may be prone to error and difficult to interpret.

The macromolecule nomenclature makes use of the following abbreviations:

| Abbreviation | Name | Structure[1] |
| --- | --- | --- |
| NEOEOEN | 2-[2-(2-aminoethoxy)ethoxy]-ethylamine | |
| [CBz]NEOEOEN | Benzyloxycarbonylamino-3,6-oxa-8-aminooctane | |
| [Boc]NEOEOEN | t-butoxycarbonylamino-3,6-oxa-8-aminooctane | |
| Su(NPN)$_2$ | | |
| Lys | Lysine | |

-continued
| Abbreviation | Name | Structure[1] |
|---|---|---|
| DBL-OPNP | p-nitrophenyl active ester of di-Boc Lysine | 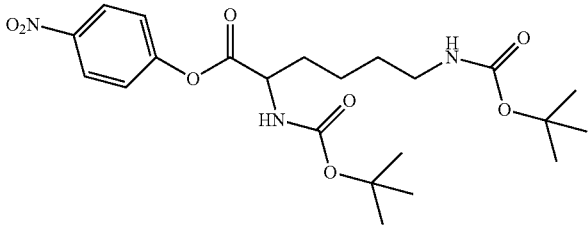 [SMILES: CC(C)(C)OC(=O)NCCCCC(NC(=O)OC(C)(C)C)C(=O)Oc1ccc([N+](=O)[O-])cc1] |
| NH₂•TFA | | Represents the surface amine groups of the deprotected molecule as the TFA salt |
| Boc | t-butyloxycarbonyl | 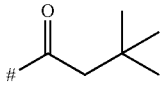 |
| CBz | Benzyloxycarbonyl | 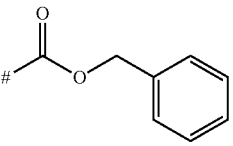 |
| p-NO₂—CBz | p-nitro-benzyloxycarbonyl | 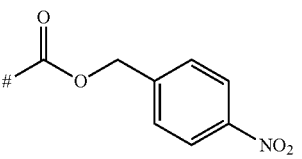 |
| (NPN)₂ [CBz]₂ | | 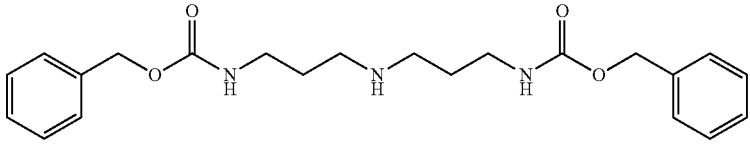 [SMILES: O=C(NCCCNCCCNC(=O)OCc1ccccc1)OCc1ccccc1] |
| (NPN)₂ [Boc]₂ | | 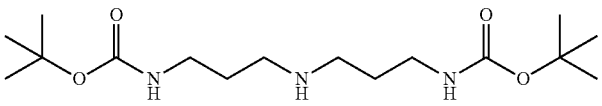 [SMILES: CC(C)(C)OC(=O)NCCCNCCCNC(=O)OC(C)(C)C] |
| HO-Su(NPN)₂ [CBz]₂ | | 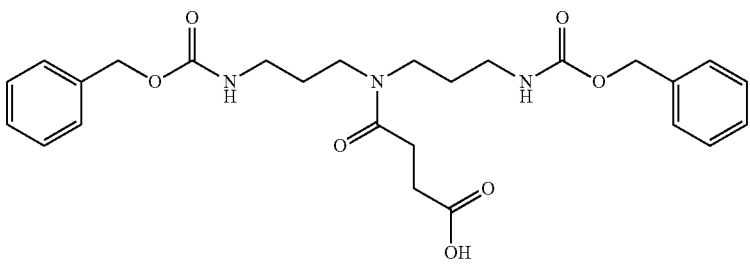 [SMILES: O=C(O)CCC(=O)N(CCCNC(=O)OCc1ccccc1)CCCNC(=O)OCc1ccccc1] |
| HO-Su(NPN)₂ [Boc]₂ | | 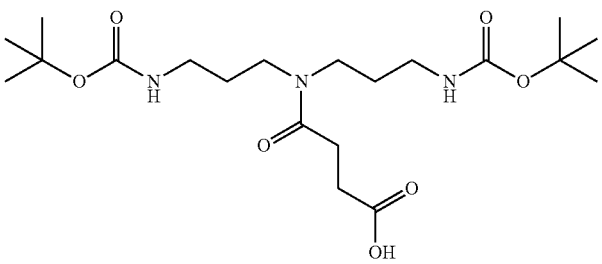 [SMILES: CC(C)(C)OC(=O)NCCCN(CCCNC(=O)OC(C)(C)C)C(=O)CCC(=O)O] |

| Abbreviation | Name | Structure[1] |
|---|---|---|
| PNPO-Su(NPN)$_2$ [CBz]$_2$ | | 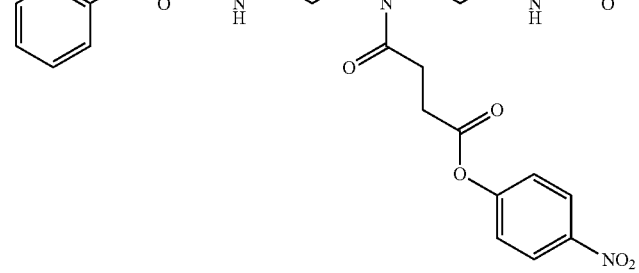 |
| PNPO-Su(NPN)$_2$ [Boc]$_2$ | | 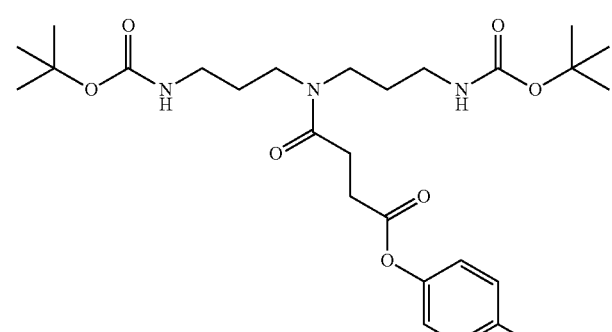 |
| MeOGly•HCl | | 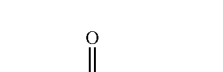 |
| PNPO-α-Boc-ε-CBz-Lys | | 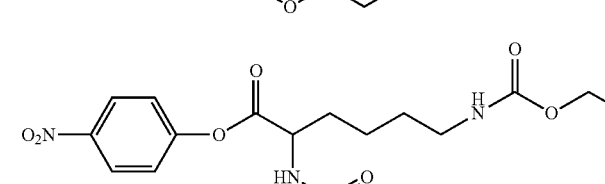 |

Further abbreviations are as follows:

| Abbreviation | Full Name |
|---|---|
| PyBop | Benzotriazole-1-yl-oxy-tris-pyrrolidino-phosphonium hexafluorophosphate |
| DIPEA | N,N-Diisopropylethylamine |
| TEA | Triethylamine |
| DCC | 1,3-Dicyclohexylcarbodiimide |
| HOBt | 1-Hydroxybenzotriazole hydrate |
| DMAP | 4-(Dimethylamino)pyridine |
| NHS | N-hydroxysuccinimide |
| TFA | Trifluoroacetic acid |
| DCM | Dichloromethane |
| EtOAc | Ethyl acetate |
| MeCN | Acetonitrile |
| DMF | Dimethylformamide |
| THF | tetrahydrofuran |
| N$_3$ | Azide |
| MAL | maleimide |
| BCN | Bicyclo[6.1.0]nonyne containing linker |
| DBCO | dibenzylcyclooctyne containing linker |
| UPA | A dendrimer with a selected point of attachment at which a linker or pharmaceutically active agent is or can be attached |

HPLC MS (Mass Spectrometry) and NMR equipment details:

HPLC—Waters 2795 with 2996 Diode Array Detector (DAD)

MS—Waters ZQ4000 with ESI probe, inlet flow split to give around 50 µL/min to the MS.

Mass Spectra data was acquired in positive or negative electrospray ionisation mode as indicated. The raw data was deconvoluted using a Maximum Entropy algorithm (Max-Ent) as implemented in MassLynx software v4.0, supplied by Waters Corporation. The data reported in the experimental details corresponds to the observed value after deconvolution to a theoretical zero charge state.

NMR—300 MHz Bruker,

Preparation of carboxy reactive dendrimer scaffolds have been previously described in particular in WO2008/017125. Examples A and B are provided as a general methods for pegylation of any size, and protein conjugation. One skilled in the art can adapt these methods to prepare the various dendrimers outlined herein In examples A, B, I, J and K the reference to [Lys] in a formula is reference to the lysine building units on the surface layer of the dendrimer.

Example A. Pegylation of Dendrimer Scaffold $HO_2C-PEG_{12}-UPA[Lys]_{16}[PEG_8]_{32}$ To a stirred solution of mPEG$_8$-CO$_2$H (843 mg) in DMF (7 mL) under an atmosphere of N$_2$ at ambient temperature were added NMM (1.24 mL) and PyBOP (0.9 equivalents). After 30 min, a solution of HO$_2$C-PEG$_{12}$-UPA-[Lys]$_{16}$[NH$_2$.TFA]$_{32}$ (377 mg) in DMF (8 mL) was added and the ensuing reaction mixture left to stir for 16 h. The reaction mixture was diluted with Milli Q water (80 mL) and the resulting solution filtered through a 0.45 μm acrodisc filter. The resulting filtrate was subjected to ultrafiltration using a 5 kDa minimate membrane. The collected retentate was lyophilised to give a pale yellow sticky solid (495 mg, 64%). $^1$H-NMR (300 MHz, D$_2$O) δ (ppm) 1.26-1.92 (m, 184H); 2.52-2.71 (m, 74H); 3.18-3.24 (m, 62H); 3.42 (s, 96H); 3.64-3.87 (m, 1042H); 4.19-4.36 (m, 29H). LCMS (philic method, formic acid buffer) R$_t$=10.41 min. ESI MS (+ve) 2192 [M+8H]$^{8+}$/8, 1949 [M+9H]$^{9+}$/9, 1754 [M+10H]$^{10+}$/10. Transforms to 17 529.

Example B1 NHS Conjugation of Dendrimer to Insulin

Insulin-NHCO-PEG$_{12}$-UPA[Lys]$_{16}$[PEG$_8$]$_{32}$

To a stirred solution of HO$_2$C-PEG$_{12}$-UPA-[Lys]$_{16}$[PEG$_8$]$_{32}$ (250 mg) (as prepared in WO2008/017125, example 2 iii.) and TSTU (1.1 equivalents) in DMF (4.5 mL) was added NMM (5 μL). The ensuing reaction mixture was left to stir at ambient temperature for 30 min, then added slowly to an ice-cooled, gently stirred solution of insulin (125 mg) in carbonate buffer (4.5 mL, pH 10.5). The ensuing reaction mixture was left to stand for 15 min, the pH lowered to pH 7 by the slow addition of 1M HCl. The resulting opaque white suspension (insulin precipitated) was diluted with Milli Q water then lyophilised to give an off-white sticky solid.

The lyophilised material was taken up in Milli Q water and centrifuged (4° C., 13 200 rpm, 10 min) and the supernatant collected. This centrifugation procedure was repeated and the combined supernatant material was lyophilised. The lyophilised material was dissolved in Milli Q water and filtered through a 0.45 μm acrodisc filter then purified by preparative HPLC; 27-40-70% MeCN, 214 nm, 0.05% formic acid to give a fluffy white solid (68.8 mg, 21%). LCMS (philic method, formic acid buffer) R$_t$=8.62 min. ESI MS (+ve) 2916 [M+8H]$^{8+}$/8, 2592 [M+9H]$^{9+}$/9; 2333 [M+10H]$^{10+}$/10, 2121 [M+11H]$^{11+}$/11, 1944 [M+12H]$^{12+}$/12, 1795 [M+13H]$^{13+}$/13, 1667 [M+14H]$^{14+}$/14, 1556 [M+15H]$^{15+}$/15. Transforms to 23 319. Further analysis of the conjugates was carried out using SDS-Page as well as trypsin digest to confirm the dendrimer had been conjugated to the desired B-29 position of lysine.

Example B2. Click Conjugation of Insulin to Dendrimer

1. Insulin-PEG$_{12}$-N$_3$ (Insulin-Linker Precursor)

To a gently stirred solution of insulin (240 mg) in carbonate buffer (pH 10.5, 10 mL) at ambient temperature was added a solution of NHS-PEG$_{12}$-N$_3$ (23 mg) via syringe pump at a rate of 0.3 mL/min. Once addition completed, stirring ceased and the reaction mixture left to stand for 45 min. The reaction mixture was then diluted with Milli Q water (40 mL) and filtered through a 0.45 μm acrodisc filter. The resulting filtrate was subjected to ultrafiltration using a 5 kDa minimate membrane. The collected retentate was lyophilised to give a fluffy white solid.

Analysis showed ca. 60% conversion to target insulin-PEG$_{12}$-N$_3$ and ca. 40% unreacted insulin, material was used directly in the next step. LCMS (philic method, formic acid buffer) R$_t$=6.09 (insulin); R$_t$=11.62 (insulin-PEG$_{12}$-N$_3$). ESI MS (+ve) for insulin-PEG$_{12}$-N$_3$: 1609 [M+4H]$^{4+}$/4, 1287 [M+5H]$^{5+}$/5, 1068 [M+6H]$^{6+}$/6, 916 [M+7H]$^{7+}$/7. Transforms to 6432.

2. Insulin-z-QG-EDA-BCN (Alternative Insulin-Linker Precursor)

The BCN reactive dipeptide was prepared using standard peptide coupling conditions using the dipeptide z-QG-EDA-NH2 (Zedra, Cat # COO1) and BCN-NHS (Synaffix, Cat # SX-A-1028).

To a solution of Tris buffer (pH 7.5, 200 μL) was added a solution of Insulin (200 μg, 34.4 nmol) in PBS buffer (pH 7.3, 80 μL) followed by z-QG-EDA-BCN (200 μg, 360 nmol) in DMSO (80 μL). To the reaction mixture was added a solution of Transglutaminase (0.5 IU, Zedira, product # T001) in water (10 μL). The reaction was diluted with a further addition of water (30 μL) and the ensuing mixture incubated at 38° C. for 16 hours to afford the target molecule (ca. 67% conversion). LCMS (Philic method, formic acid buffer) Rt=7.75 min (Insulin), ESI MS 5808; Rt=8.53 min (Mono-BCN-Insulin conjugate) ESI MS 6346 (Max. Ent.)

3. Insulin-BCN

To a magnetically stirred solution of Insulin (5 mg, 0.86 μmol) in carbonate buffer (pH 10.5, 0.2 mL) at ambient temperature was slowly added a solution of NHS-BCN (0.25 mg, 0.86 μmo, Synaffix Product # SX-A-1028) in Acetonitrile (0.2 mL). The ensuing mixture was incubated at room temperature for 15 minutes. Analysis of the crude reaction mixture by LCMS (Philic method, formic acid buffer) confirmed the presence of the following components; R$_t$=7.75 min (Insulin), ESI MS 5808 (Max. Ent.); R$_t$=8.40 min (Mono-BCN-Insulin conjugate) ESI MS 5986 (Max. Ent.); R$_t$=9.00 min (Bis-BCN-Insulin conjugate) ESI MS 6164 (Max. Ent.). Composition of the mixture was found to be 64.8% mono-BCN-Insulin and 19.3% Bis-BCN-Insulin as determined by LCMS-UV integration, thus the total mole of reactive BCN was approximately 0.89 μmol.

4. DBCO-PEG$_8$-UPA[Lys]$_{32}$[PEG$_8$]$_{64}$ (Dendrimer Precursor)

To a stirred solution of DBCO-CO$_2$H (Product number # A101, Click Chemistry Tools, 21 mg, 3 equivalents) in DMF (1 mL) under an atmosphere of N$_2$ at ambient temperature were added NMM (10 μL) and PyBOP (17 mg, 1.5 equivalents). After 90 min, a solution of H$_2$N-PEG$_8$-UPA-[Lys]$_{32}$[PEG$_8$]$_{64}$ (700 mg, 1 equivalent) in DMF (5 mL) was added and the ensuing reaction mixture stirred for 16 h. The reaction mixture was diluted with Milli Q water (60 mL) and the resulting solution filtered through a 0.45 μm acrodisc filter. The resulting filtrate was subjected to ultrafiltration using a 5 kDa minimate membrane. The collected retentate was lyophilised to give a pale yellow/orange viscous oil (685 mg, 97%). $^1$H-NMR (300 MHz, D$_2$O) δ (ppm) 1.08-2.02 (m, 376H); 2.51-2.74 (m, 134H); 3.08-3.27 (m, 125H); 3.33-3.50 (m, 217H); 3.53-3.99 (m, 1945H); 4.15-4.39 (m, 60H). LCMS (philic method, formic acid buffer) R$_t$=10.85 min. ESI MS (+ve) 3431 [M+10H]$^{10+}$/10, 3119 [M+11H]$^{11+}$/11, 2859 [M+12H]$^{12+}$/12. Transforms to 34 295.

5. Insulin-PEG$_n$-triazoloDBCO-PEG$_8$-UPA[Lys]$_{32}$[PEG$_8$]$_{64}$

To a gently stirred solution of DBCO-PEG$_8$-UPA-[Lys]$_{32}$[PEG$_8$]$_{64}$ (680 mg) in water (5 mL) was added a solution of insulin/insulin-PEG$_{12}$-N$_3$ (40:60; 159 mg, ca. 14.8 μmol of azide) in water (6 mL). The ensuing reaction mixture was left to stand (stirring ceased) at ambient temperature for 16 h then lyophilised. The lyophilised material was dissolved in water (9 mL) and filtered through a 0.45 μm acrodisc filter then purified by preparative HPLC; 28-42-80% MeCN, 214 nm, 0.05% formic acid to give a fluffy white solid (183.8 mg, 23%). LCMS (philic method, formic acid buffer) R$_t$=9.40 min ESI MS (+ve) 3703 [M+11H]$^{11+}$/11, 3395 [M+12H]$^{12+}$/12, 3134 [M+13H]$^{13+}$/13, 2910 [M+14H]$^{14+}$/14, 2716 [M+15H]$^{15+}$/15, 2547 [M+16H]$^{16+}$/16, 2397 [M+17H]$^{17+}$/17, 2264 [M+18H]$^{18+}$/18, 2145 [M+19H]$^{19+}$/19. Transforms to 40 730. NB: Further analysis of the conjugates was carried out using SDS-Page as well as trypsin digest to confirm the dendrimer had conjugated to the desired B-29 position of lysine.

Example C. Dendrimers

The following insulin polylysine dendrimer macromolecules were made according to the methods described in WO2008/017125 examples 1 xviii, 2 iv and 4 xiii and using the conjugation methods described above in examples A and B, using different sizes of PEG and different size dendrimers.

| Compound No. | No. of Generations | Surface PEG size (PEG units) | Linker PEG size (PEG units) | % PEG (w/w) | Theoretical average MW |
|---|---|---|---|---|---|
| 1 | 2 | 4 | 12 | 32% | 9292 |
| 2 | 3 | 4 | 12 | 39% | 12064 |
| 3 | 2 | 12 | 12 | 47% | 12112 |
| 4 | 4 | 2 | 12 | 23% | 14789 |
| 5 | 3 | 8 | 24 | 50% | 15862 |
| 6 | 3 | 12 | 9 | 57% | 17585 |
| 7 | 4 | 4 | 12 | 46% | 17606 |
| 8 | 4 | 4 | 20 | 46% | 18362 |
| 9 (Example B1) | 4 | 8 | 12 | 59% | 23319 |
| 10 | 4 | 8 | 24 | 59% | 24224 |
| 11 | 4 | 12 | 12 | 66% | 28957 |
| 12 | 4 | 12 | 24 | 66% | 29858 |
| 13 (Example B2(5)) | 5 | 8 | 20 | 65% | 40725 |
| 14 | 5 | 8 | 24 | 65% | 40901 |
| 15 | 3 | Trident (4 + 3 × 12) | 12 | 83% | 45508 |
| 16 | 4 | 24 | 12 | 79% | 45873 |
| 17 | 4 | 24 | 16 | 79% | 46380 |
| 18 | 4 | 24 | 20 | 79% | 46556 |
| 19 | 5 | 12 | 12 | 73% | 51320 |
| 20 | 4 | Trident (4 + 3 × 4) | 20 | 81% | 51329 |
| 21 | 4 | Trident (4 + 3 × 12) | 24 | 88% | 51552 |
| 22 | 6 | 4 | 24 | 57% | 51842 |
| 23 | 5 | 12 | 23 | 73% | 52180 |
| 24 | 5 | 12 | 24 | 73% | 52224 |
| 25 | 6 | 4 | 36 | 57% | 52323 |
| 26 | 6 | 8 | 16 | 70% | 73997 |
| 27 | 6 | 8 | 24 | 70% | 74350 |
| 28 | 6 | 8 | 36 | 70% | 74878 |
| 29 | 4 | Trident (4 + 3 × 12) | 12 | 88% | 84421 |
| 30 | 5 | 24 | 12 | 84% | 85152 |
| 31 | 5 | 24 | 16 | 84% | 85659 |
| 32 | 5 | 24 | 24 | 84% | 86011 |

Example D. In Vitro Studies

In Vitro Binding Studies

Insulin Receptor binding assays were performed on P1 membranes prepared from stably transfected cells over-expressing the human insulin receptor (hIR) using methods known in the art, (for example, WO 2009/152128). Binding affinities were determined from a competitive radio-ligand binding assay using either human recombinant (3-[125] iodotyrosyl A14)-Insulin The assay was performed with a SPA method using PVT PEI-treated Type A wheat germ agglutinin-coupled SPA beads. IC50 values was determined from non-linear regression analysis. The affinity constant (Ki) is calculated from the IC50 value based upon the equation Ki=1C50/(1+D/Kd) where D equals the concentration of radioligand used in the experiment and Kd equals the equilibrium binding affinity constant of the radioligand determined from saturation binding analysis.

These data show that macromolecules of the present invention have reduced hIR affinity, making these weak agonists of the hIR under these conditions.

Whole Cell Assay

The compounds of the present invention may be evaluated for functional activity using well known methods such as heterogeneous time-resolved fluorometric assay method (for example, DELFIA®, Perkin-Elmer) and using commercially available Anti-insulin receptor A-chain mAb 8314 ELISA assays (Abcam, Inc., Cambridge) using methods known in the art, (for example, WO 2009/152128). The potencies of the insulin analogs are calculated as the EC50.

| Compound No | MW | hIR- A Binding Assay 1 (Ki nM) | hIGF1 R Binding Assay 2 (Ki nM) | cell based promoter reporter assay 1 (EC50 nM) | cell based phosphorylation assay 2 (EC50 nM) | cell based proliferation assay 3 (EC50 nM) |
|---|---|---|---|---|---|---|
| human insulin | 5800 | 0.24 | 0.22 | 0.0277 | 3.4 | 2.8 |
| 5 | 15862 | 6.8 | 11.9 | 0.36 | 44 | 80.3 |
| 9 | 23319 | 4.6 | 10.6 | 0.57 | 32.3 | 51.5 |

-continued

| Compound No | MW | hIR- A Binding Assay 1 (Ki nM) | hIGF1R Binding Assay 2 (Ki nM) | cell based promoter reporter assay 1 (EC50 nM) | cell based phosphorylation assay 2 (EC50 nM) | cell based proliferation assay 3 (EC50 nM) |
| --- | --- | --- | --- | --- | --- | --- |
| 10 | 24224 | 3.6 | 5.5 | 0.2 | 26 | 32 |
| 12 | 29858 | 10.5 | 8 | 0.25 | 39.9 | 80.2 |
| 13 | 40725 | 8.6 | 12.3 | 0.22 | 32.1 | 63.8 |
| 14 | 40901 | 13.5 | 15 | 0.28 | >200 | 49.8 |
| 17 | 46380 | 25.5 | 28.9 | 1.58 | >200 | 89.3 |
| 18 | 46556 | 10 | 27.4 | 0.43 | 35.1 | >200 |
| 20 | 51329 | 24.8 | 19.3 | 0.56 | | 63.1 |
| 21 | 51552 | 28.5 | 24.4 | 0.74 | 366.4 | 184 |
| 22 | 51842 | 2 | 3.1 | 0.26 | 14 | 46.3 |
| 25 | 52323 | 2.6 | 2.9 | 0.3 | 26.6 | 28.1 |
| 26 | 73997 | 41.2 | 42.5 | 1.77 | >200 | 176 |
| 27 | 74350 | 19 | 21.3 | 0.76 | 61.3 | 85 |
| 28 | 74878 | 3.1 | 4.3 | 0.37 | 44.6 | 47.8 |
| 31 | 85659 | 64 | >84.8 | 1.2 | 93.1 | 112 |
| 32 | 86011 | 44.6 | 40.6 | 1.17 | 151.7 | 103.7 |

Example E. PD & PK

Determination of Glucose PD and Insulin PK in Diabetic Rats.

Male, normal SD rats at 10 weeks of age 250-280 g body weight were rendered diabetic by a single injection of 45 mg/kg streptozotocin (STZ) in 0.5 M Citric Acid, pH 4.5 dosed intravenously into their tail vein, three days prior to study start. At the start of the study animals were sorted into groups based on body weight and blood glucose (n=6 per group) and only rats with between 400 and 550 mg/dl blood glucose were included in the study. Each group of animals receive a single subcutaneous injection of the test compound at one of two doses (low dose 167 nmol/kg and high dose of 500 nmol/kg). Within each set of experiments two additional dosing groups of animals were included; vehicle control (negative control) and determir (positive control) dosed at 568 nmol·kg. Within each dosing group duplicate blood samples were periodically drawn from the tail vein and collected into tubes containing disodium EDTA. Blood glucose levels were measured with a glucometer. Also, plasma was collected by vein blood sampling and a commercially available rat insulin radioimmunoassay was used to determine the levels of the administered drug in the plasma. The results from these experiments are shown in the Blood Glucose Curves and Serum Insulin curves FIGS. 1-6. All compounds were able to initially suppress blood glucose in STZ-treated rats to 100 mg/dL or below, a level that is observed with an effective dose of insulin in this model. The positive control, insulin detemir was shown to suppress blood glucose for 5-6 hours in the above assay with a 568 nmol/kg single dose. Normal blood glucose in this model is generally observed at between 400-600 mg/dL, as observed in vehicle control animals The pharmacokinetic results for compound 5 (15.9 kDa), FIG. 1, indicated a time to minimal glucose concentration (glucose nadir) of about 4 h and blood glucose suppression below 100 mg/dL to about 13 hours. Blood glucose had returned to normal levels by 24 hours for both low and high doses, similar to detemir. By comparison with detemir, compound 5 would be expected to be capable of acting as a human daily basal insulin.

Figure 2:
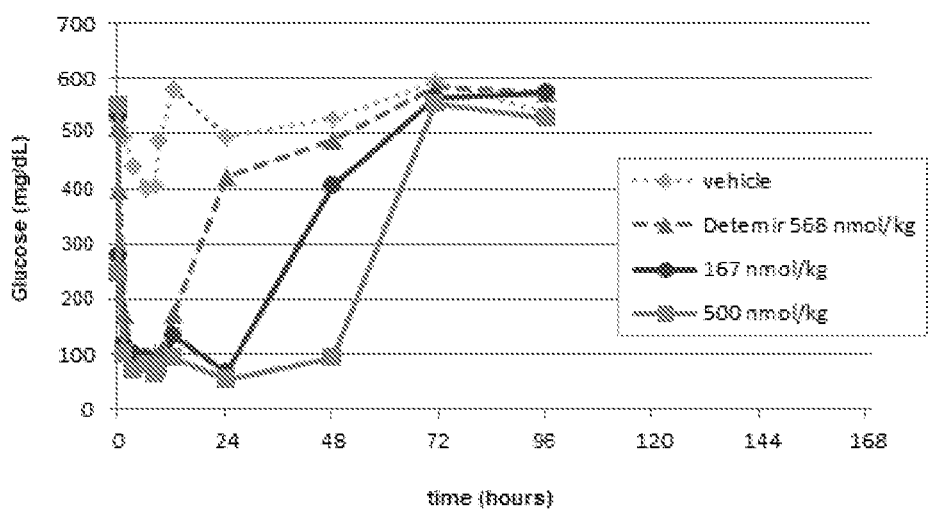
FIG. 2 provides a graph showing glucose (mg/dL) versus time for compound 9.

The pharmacokinetic results for compound 9 (23.3 kDa), FIG. 2, indicated a time to minimal glucose concentration (glucose nadir) of about 4 h and blood glucose suppression below 100 mg/dL to about 24 and 48 hours for low and high dose respectively. Blood glucose had returned to normal levels by 72 hours for both low and high doses.

Figure 3:
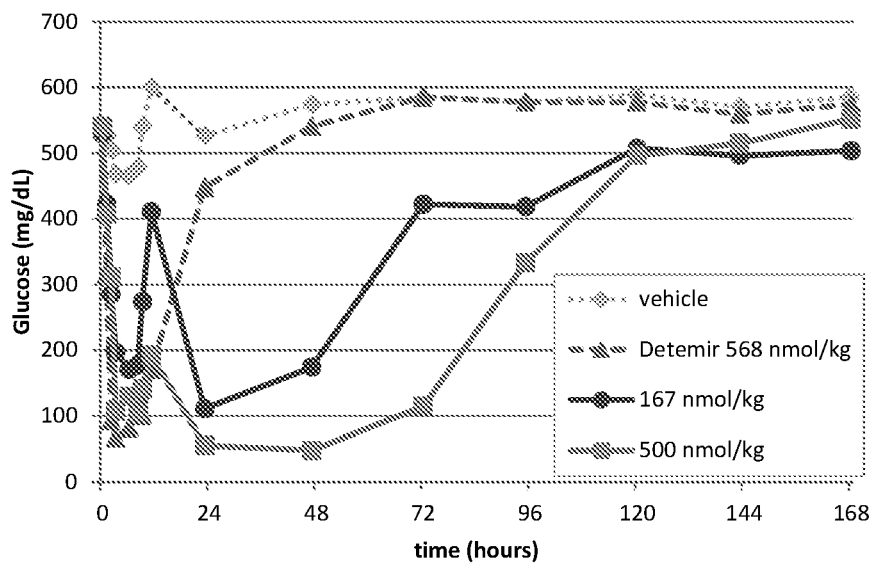
FIG. 3 provides a graph showing glucose (mg/dL) versus time for compound 14.

The pharmacokinetic results for compound 14 (40.9 kDa), FIG. 3, indicated a time to minimal glucose concentration (glucose nadir) of about 4-24 h and about 4-48 h for low and high doses respectively and blood glucose suppression below 100 mg/dL to about 24 and 72 hours for low and high dose respectively. Blood glucose had returned to normal levels by 120 hours for both doses. Determining the glucose nadir was complicated by a spike in glucose levels due to rats intensively feeding to counter the low level of glucose induced by the test article. Results from the serum insulin curves (FIG. 9) show an elimination half-life ($T_{1/2}$) of about 15 h, Tmax of about 24 h, a Cmax of 75 and 380 nM for the low and high dose respectively and an apparent clearance rate of (CL/F) ranging from 41-67 mL/h/kg.

Figure 4:
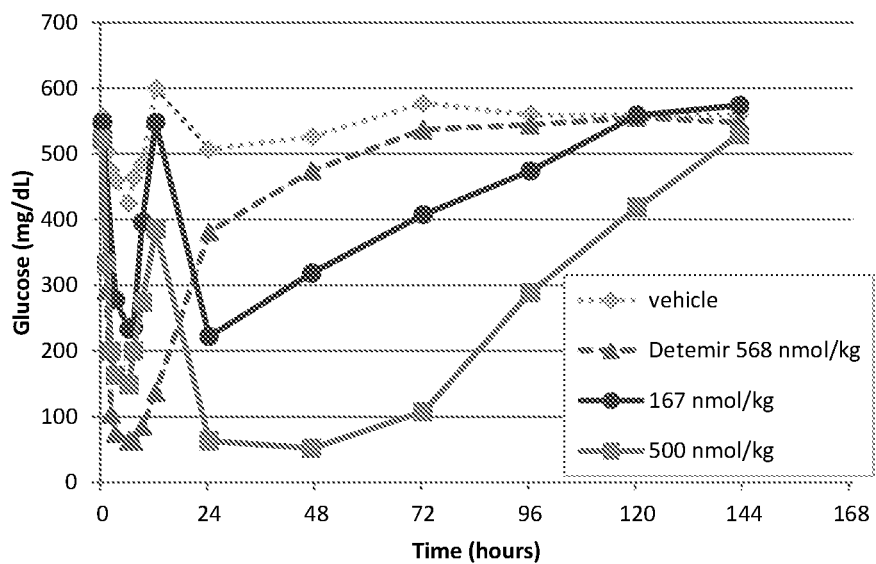
FIG. 4 provides a graph showing glucose (mg/dL) versus time for compound 20.

The pharmacokinetic results for compound 20 (51.3 kDa), FIG. 4, indicated a time to minimal glucose concentration (glucose nadir) of about 4-48 h and blood glucose suppression below 100 nmg/dL to about 72 hours for the high dose. Whilst the lower dose only suppressed glucose to a level of about 200 mg/dL the rate of return to normal glucose levels was significantly slower than the smaller test articles, compounds 5, 9 and 14. Blood glucose had returned to normal levels by 120 and 144 hours for the low and high doses respectively. The glucose nadir was complicated by a spike in glucose levels due to rats intensively feeding as described above. Results from the serum insulin curves show a Tmax of about 24 h (FIG. 9).

Figure 5:
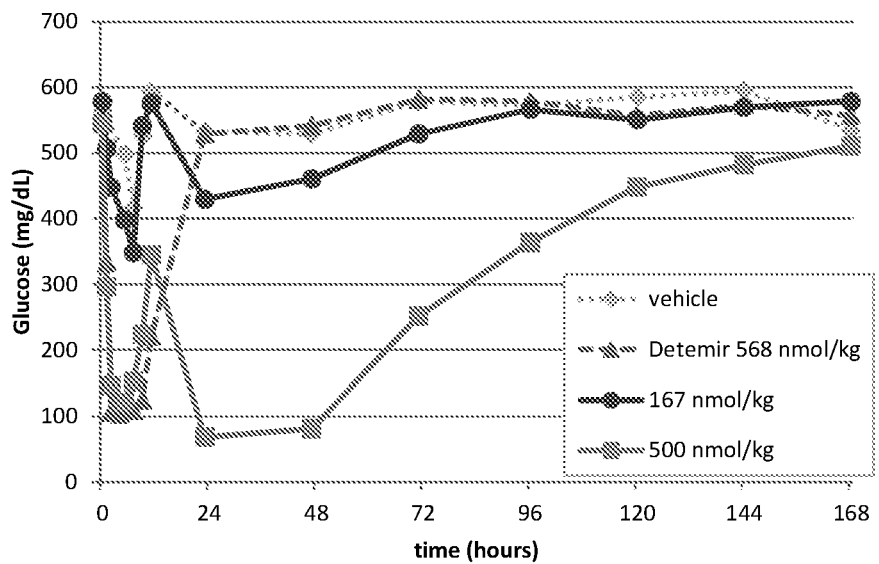
FIG. 5 provides a graph showing glucose (mg/dL) versus time for compound 28.

The pharmacokinetic results for compound 28 (75 kDa), FIG. 5, indicated a time to minimal glucose concentration (glucose nadir) of about 4-24 h and blood glucose suppression below 100 mg/dL to about 48 hours for the high dose. Blood glucose had returned to normal levels by about 144 hours for the high dose. The glucose nadir was complicated by a spike in glucose levels due to rats intensively feeding as described above. Results from the serum insulin curves show a Tmax of about 24 h (FIG. 9).

Figure 6:
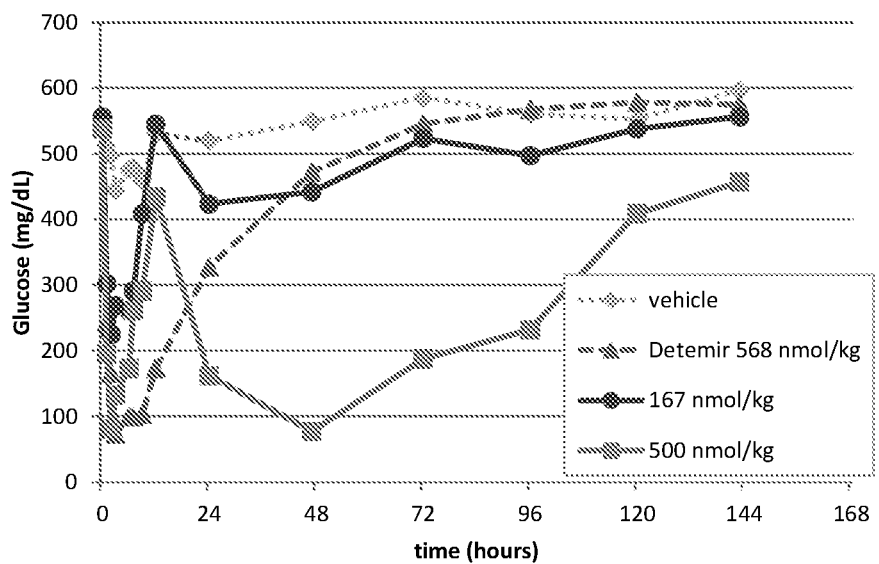
FIG. 6 provides a graph showing glucose (mg/dL) versus time for compound 32.

The pharmacokinetic results for compound 32 (86 kDa), FIG. 6, indicated a time to minimal glucose concentration (glucose nadir) of about 4-48 h and blood glucose suppression below 100 mg/dL up to about 48 hours for the high dose with a very slow rise back to normal levels. Blood glucose had not yet returned to normal levels by 144 hours for the high dose (500 nmol/kg). The glucose nadir was complicated by a spike in glucose levels due to rats intensively feeding as described above. Results from the serum insulin curves show a Tmax of about 48 h (FIG. 9).

Figure 8:
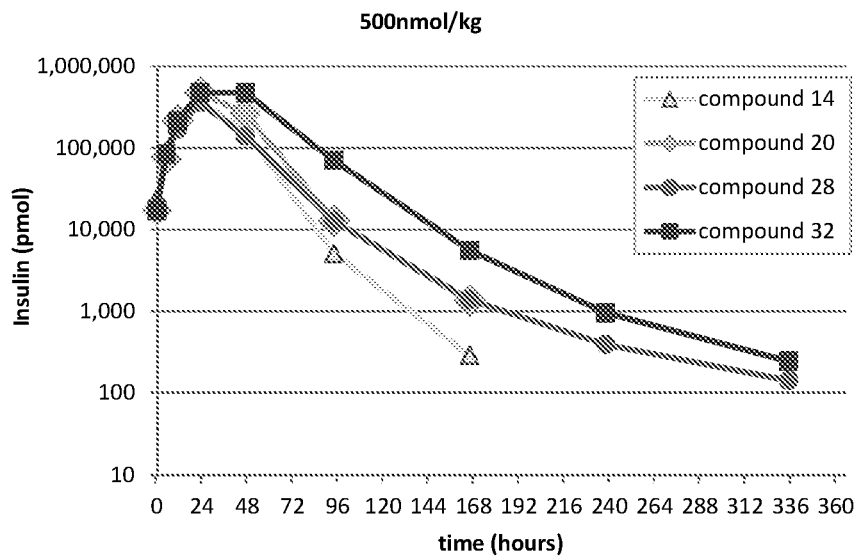
FIG. 8 provides a graph showing comparison of mean serum insulin for compounds 14, 20, 28, and 32.

FIG. 8 shows a comparison of the insulin profile of compounds 14, 20, 28 and 32 for 500 nmol/kg dose. It can be observed that the T max and T½ increases with increasing size.

FIG. 9 shows a comparison of the glucose profile of compounds 5, 9, 14, 20, 28 and 32 for 500 nmol/kg dose. It can be observed that compounds 14, 20, 28 and 32 have a similar profile, except that the initial response to administration of the test article is varied Smaller compounds 5 and 9 show almost no spike, but do not have the extensive duration of action. The larger the macromolecule, the more pronounced the feeding spike at approximately 12 hours. It is hypothesized that the larger size macromolecule acts less rapidly to counter the feeding spike.

TABLE E1

| Compound No | T ½ (hr)* | | Normalised Area over the curve (g/dL · h)# | |
|---|---|---|---|---|
| | 167 nmol/kg | 500 nmol/kg | 166 nmol/kg | 500 nmol/kg |
| Compound 5 | | | 3.9 | 5.6 |
| Compound 9 | | | 16.3 | 25.2 |
| Compound 14 | 17 | 13 | 23.0 | 37.5 |
| Compound 20 | 18 | 16 | 16.4 | 36.4 |
| Compound 28 | 21 | 18 | 3.6 | 32.0 |
| Compound 32 | 21 | 19 | 4.9 | 32.8 |

*calculated with data points to 166 hours
calculated with data points to 96 hours Table E1 shows plasma half-life of insulin for a selection of the compounds made and tested. Half-life is shown to be greater than 13 hours for these macromolecules for time points out to 166 hours, and as high as 21 hours for compound 28. However when all available data is analysed (to time 336 hours), the terminal plasma $T_{1\!/\!2}$ of compound 28 is 50 and 52 hours and for compound 32 is 43 and 38 hours calculated for the 167 nmol/kg and 500 nmol/kg doses respectively.

Table E1 also shows normalised area over the curve for glucose, calculated as follows:

$$\text{Normalised Area over curve} = \sum_{i=1}^{i=n-1} (x_{(i+1)} - x_i)(R - (y_i + y_{(i+1)})/2)$$

Where R is the normalisation constant, being the average glucose level in the vehicle group and x and y are the time and glucose data points. Area over the curve shows the greatest glucose control for compounds of about 40 kda or greater (compounds 14, 20, 28 and 32), and more specifically compounds 14 and 20, which show the least post dose glucose spike.

Example F. Toxicity

Repeat Dose Toxicity and Toxicokinetics

Male, normal SD rats at 10 weeks of age 250-280 g body weight were randomised into dosing groups (n=17 per dosing group, with 5 animals used for toxicity assessments and 12 animals used for toxicokinetics (TK) and glucodynamics). Each group of animals received a subcutaneous injection of Compound 20 every second day for a total of 31 days. The dosing groups for the experiment were 0, 1.6, 4.8 and 16 mg/k of test article per dose, every second day for a total of 16 doses or 32 days. Each animal was observed for survival, clinical signs such as body weight (BW), food consumption (FC), clinical pathology, as well as morphological pathology. Within the TK/glucodynamics groups blood samples were periodically drawn from the tail vein and collected into tubes containing disodium EDTA. Blood glucose levels were measured with a glucometer.

Results from the study showed no mortality at any dose, no treatment-related clinical signs and no BW/FC effects. Morphologic pathology observations: At the highest dose group (16 mg/kg) some expected sub-clinical pathology was observed and was considered to be secondary to hypoglycaemia due to the significantly high repeated doses of insulin administered. At the two high doses (4.8 and 16 mg/kg) some observations of minor injection site changes were noted and once again considered insignificant and secondary to injection site effects.

Figure 7A:
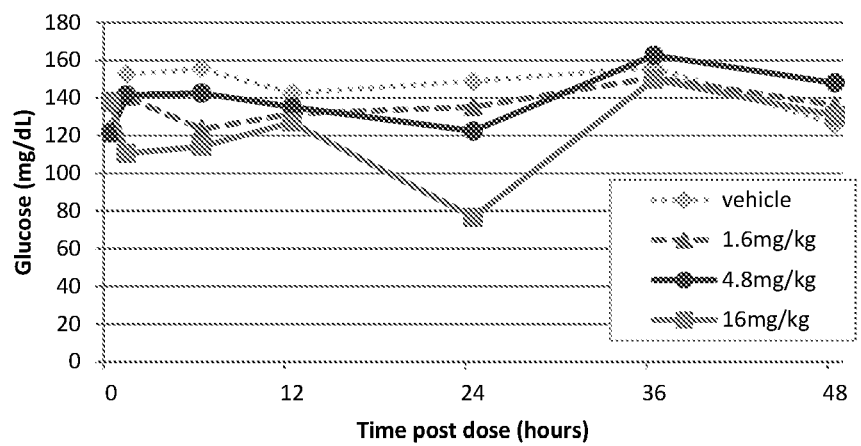
FIG. 7A provides a graph showing mean serum glucose concentration at days 1-3 for compound 20.
Figure 7B:
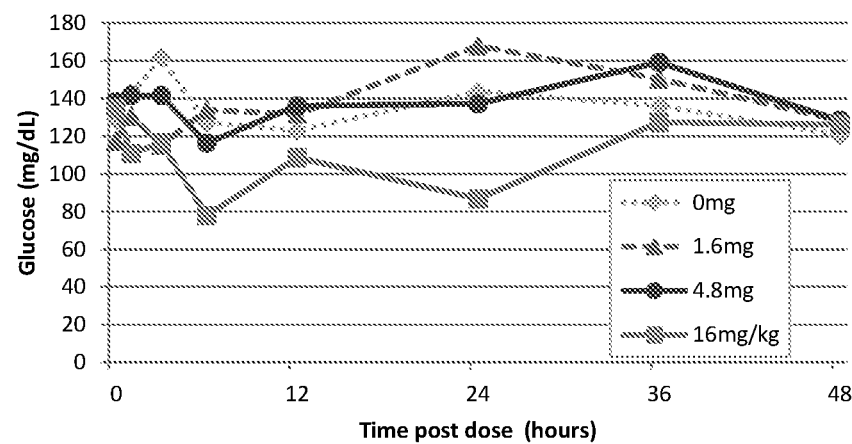
FIG. 7B provides a graph showing mean serum glucose concentration at days 29-31 for compound 20.

Clinical pathology: Glucodynamic test animals at both the beginning (days 1-3) and end of the study (days 29-31) responded to the highest dose of 16 mg/kg with a <50% reduction in serum glucose which returned to baseline by 36 h. No reduction compared to control was observed for the other two doses 1.6-4.8 mg/kg. See FIGS. 7A and 7B Mean serum glucose concentrations (Days 1-3 and 29-31 respectively). This result indicates that repeat dosing of compound 20 under extremely high dose levels under an aggressive dosing regimen did not result in the development of insulin resistance. In certain embodiments the present invention may delay or prevent disease progression.

Example G. Solubility

The aqueous solubility of compounds was determined by dissolving an accurately weighted sample of lyophilised product in a known amount of Milli Q water within a 30 minute time period to form a clear colourless solution that was non-viscose and could be easily withdrawn by pipette.

Compound 6: 480 mg/mL (158 mg/ml of insulin equivalents).

Compound 8: >249 mg/mL (79 mg/ml of insulin equivalents).

Compound 20: >243 mg/mL (>27 mg/ml of insulin equivalents).

Example H. Stability

Compounds 20 and 32 were examined for longer term stability studies. For each compound stock samples were prepared, the first as dry material and the second as aqueous solutions in PBS (pH 7.4, 1 mg/mL). Each stock sample was either weighted out or aliquoted into ~45 storage sample vials containing roughly 1 mg of conjugate per vial. The sets of vials were sealed and then divided into three storage temperatures (~20° C., 4° C. and ambient temperature). At various time-points of T=0, 2 weeks, 1, 3 and 6 month three samples were taken from storage (note: dry samples were made up to 1 mg/mL with MilliQ water just prior to LCMS analysis). Samples were analysed by LCMS to determine overall stability and to observe whether insulin had cleaved from the dendrimer or whether any other significant changes had occurred.

At the end of the study, under the conditions of the experiment, no change over time was observed between the different storage temperatures or conditions.

Example I α-Melanocyte-Stimulating Hormone (α-MSH)

NDP-α-MSH-CH$_2$CO NEOEOEN [Su(NPN)$_2$] [GlyLys]$_2$ [ε-CBz]$_2$ [Lys]$_2$ [PEG$_{570}$]$_4$, compound 33
i. [ClCH$_2$CO] NEOEOEN [Su(NPN)$_2$] [GlyLys]$_2$ [ε-CBz]$_2$ [Lys]$_2$ [PEG$_{570}$]$_4$ To a solution of [TFA.NH$_2$] EOEOEN [Su(NPN)$_2$] [GlyLys]$_2$ [ε-CBz]$_2$ [Lys]$_2$ [PEG$_{570}$]$_4$ (the preparation of this intermediate is outlined in WO2008/017125, example 4 xiv) in buffer (100 mL 0.1 M Na$_2$HPO$_4$; 100 mL 0.1 M HCl, pH ~8.5) was added chloroacetyl chloride and the reaction left stirring for 2 h, the product [ClCH$_2$CO] NEOEOEN [Su(NPN)$_2$] [GlyLys]$_2$ [ε-CBz]$_2$ [Lys]$_2$ [PEG$_{570}$]$_4$, was characterised by HPLC/MS and used immediately in the following reaction.

ii. NDP-α-MSH-CH$_2$CO NEOEOEN [Su(NPN)$_2$] [GlyLys]$_2$ [ε-CBz]$_2$ [Lys]$_2$ [PEG$_{570}$]$_4$

To an excess of mercapto-NDP-α-MSH (mercapto-Ser-Tyr-Ser-Nle-His-DPhe-Arg-Trp-Gly-Lys-Pro-Val-NH$_2$) was added a freshly prepared solution of [ClCH$_2$CO] NEOEOEN [Su(NPN)$_2$] [GlyLys]$_2$ [ε-CBz]$_2$ [Lys]$_2$ [PEG$_{570}$]$_4$, compound B, in a buffer of 0.1 M sodium hydrogen orthophosphate/0.1 M HCl (pH 8.5). After stirring at room temperature for 16 h, the conjugated product, compound 33, was detected in the reaction mixture by HPLC-MS.

Example J Alternative Core i. Azido-PEG$_{24}$-CO[N(PNBoc)$_2$]

To a stirred solution of N$_3$-PEG$_{24}$-CO$_2$H (2.00 g) and PyBOP (1.33 g) in DMF (20 mL) under an atmosphere of N$_2$ was added NMM (563 μL). After 10 min, a solution of N(PNBoc)$_2$ (622 mg) in DMF (5 mL) was added and the ensuing reaction mixture left to stir overnight at room temperature. The volatiles were removed in vacuo and the resulting oil dissolved in MeCN and purified by preparative HPLC (27-50-70% MeCN, RT 47-50 min) to give a pale yellow oily solid (1.37 g, 54%). $^1$H-NMR (300 MHz, CD$_3$OD) δ (ppm): 1.44 (m, 18H); 1.65-1.84 (m, 4H); 2.63 (t, J 6.3 Hz, 2H); 3.05 (dt, J 6.9 and 14.7 Hz, 4H); 3.36-3.41 (m, 6H); 3.60-3.78 (m, 98H). LCMS (philic method, formic acid buffer) RT=9.32 min ESI MS (+ve) 1486.3 [A]$^+$; calc. m/z for C$_{67}$H$_{132}$N$_6$O$_{29}$ [M]$^+$: 1486.8.

ii. Azido-PEG$_{24}$-CO[N(PNH$_2$.TFA)$_2$]

To an ice-cooled, stirred suspension of N$_3$-PEG$_{24}$-CO[N(PNBoc)$_2$] (1.37 g) in water (5 mL) was added TFA (6 mL). After 5 min, the ice-bath was removed and the ensuing reaction mixture left to stir at room temperature overnight. The volatiles were removed in vacuo and the remaining aqueous solution was diluted further with water (50 mL) and freeze dried to give the product as a pale yellow oil (1.67 g, 119%). $^1$H-NMR (300 MHz, D$_2$O) δ (ppm): 1.88-2.06 (m, 4H); 2.74 (t, J 6.0 Hz, 2H); 2.96 (t, J 7.2 Hz, 2H); 3.04 (apparent t, J 7.5 Hz, 2H); 3.42-3.52 (m, 6H); 3.67-3.95 (m, 93H). LCMS (philic method, TFA buffer) RT=8.47 min, ESI MS (+ve) 1286.0 [M]$^+$; calc. m/z for C$_{57}$H$_{116}$N$_6$O$_{25}$ [M]$^+$= 1286.6.

iii. Azido-PEG$_{24}$-CO[N(PN)$_2$][Lys]$_2$[Boc]$_4$ G1

To a stirred solution of N$_3$-PEG$_{24}$-CO[N(PNH$_2$.TFA)$_2$] (186 mg) in DMF (7 mL) under an atmosphere of N$_2$ was added TEA (242 μL), followed by addition of DBL-OPNP (270 mg). The ensuing reaction mixture was then left to stir overnight at room temperature. The volatiles were evaporated in vacuo and the resulting residue dissolved in MeCN and purified by preparative HPLC (30-80% MeCN, RT 33.5-36 min) to give a pale yellow oil (224 mg, 80%). $^1$H-NMR (300 MHz, CD$_3$OD) δ (ppm): 1.22-1.87 (m, 56H); 2.64 (t, J 6.0 Hz, 2H); 3.03 (t, J 6.6 Hz, 4H); 3.13-3.23 (m, 4H), 3.36-3.45 (m, 6H); 3.60-3.69 (m, 100H); 3.77 (t, J 6.0 Hz, 2H); 3.85-3.88 (m, 1H); 3.92-4.02 (m, 2H). LCMS (phobic method 4.1a, formic buffer) RT=6.74 min; ESI MS (+ve) 1942.4, [M]$^+$; calc. m/z for C$_{89}$H$_{172}$N$_{10}$O$_{35}$$^+$[1\4+H]$^+$= 1942.4.

iv. Azido-PEG$_{24}$-CO[N(PN)$_2$][Lys]$_2$[TFA]$_4$ G1

To an ice-cooled, stirred suspension of N$_3$-PEG$_{24}$-CO[N(PN)$_2$][Lys]$_2$[Boc]$_4$ (220 mg) in water (4 mL) was added TFA (4 mL). After 5 min, the ice-bath was removed and the ensuing reaction mixture left to stir at room temperature overnight. The volatiles were removed in vacuo and the remaining aqueous solution was diluted further with water (50 mL) and freeze dried to give the product as a pale yellow oil (251 mg, 111%). LCMS (philic method, formic buffer) RT=6.49 min, ESI MS (+ve) 1542.1 [A]$^+$; calc. m/z for C$_{69}$H$_{140}$N$_{10}$O$_{27}$ [M]$^+$=1541.90.

v. Azido-PEG$_{24}$-CO[N(PN)$_2$][Lys]$_4$[Boc]$_8$ G2

To a stirred solution of N$_3$-PEG$_{24}$-CO[N(PN)$_2$][LysMNH$_2$.TFA]$_4$ (117 mg) in DMF (8 mL) under an atmosphere of N$_2$ was added TEA (196 μL), followed by addition of DBL-OPNP (219 mg). The ensuing reaction mixture was left to stir overnight at room temperature. The volatiles were evaporated in vacuo to give the crude material as a pale yellow oil (167 mg, 100%). LCMS (phobic method 4.1a, formic buffer) RT=8.35 min; ESI MS (+ve) 1328.6 [M+2H]$^{2+}$/2-Boc; calc. m/z for C$_{133}$H$_{252}$N$_{18}$O$_{47}$ [M]$^+$= 2855.6.

vi. Azido-PEG$_{24}$-CO[N(PN)$_2$][Lys]$_4$[NH$_2$.TFA]$_8$ G2

To an ice-cooled, stirred suspension of N$_3$-PEG$_{24}$-CO[N(PN)$_2$][Lys]$_4$[Boc]$_8$ (167 mg) in water (4 mL) was added TFA (6 mL). After 5 min, the ice-bath was removed and the ensuing reaction mixture left to stir at room temperature overnight. The volatiles were removed in vacuo and the remaining aqueous solution was filtered through a 0.45 μm acrodisc syringe filter and purified by preparative HPLC (10-60% MeCN, 0.1% TFA buffer; RT 27-29 min) to give the product as a very pale yellow sticky solid (124 mg, 71% over 2 steps). $^1$H-NMR (300 MHz, D$_2$O) δ (ppm): 1.30-1.96 (m, 42H); 2.71 (t, J 6.0 Hz, 2H); 2.98-3.04 (m, 8H); 3.13-3.30 (m, 8H); 3.36-3.53 (m, 7H); 3.68-3.84 (m, 100H); 3.93 (t, J 6.6 Hz, 2H); 4.04 (t, J 6.6 Hz, 2H); 4.25 (t, J 7.2 Hz, 2H). LCMS (philic method, TFA buffer) RT=7.76 min, ESI MS (+ve) 1028.3 [M+2H]$^{2+}$/2, 685.9 [M+3H]$^{3+}$/3; calc. m/z for C$_{93}$H$_{190}$N$_{18}$O$_{31}$$^{2+}$ [M+2H]$^{2+}$/2: 1028.3, calc m/z for C$_{93}$H$_{191}$N$_{18}$O$_{31}$$^{3+}$ [M+3H]$^{3+}$/3: 685.9.

vii. Azido-PEG$_{24}$-CO[N(PN)$_2$][Lys]$_8$[Boc]$_{16}$ G3

To a stirred solution of N$_3$-PEG$_{24}$-CO[N(PN)$_2$][Lys]$_4$[NH$_2$.TFA]$_8$ (776 mg) in DMF (18 mL) under an atmosphere of N$_2$ was added TEA (2 mL), followed by DBL-OPNP (1.96 g). The resulting yellow reaction mixture was allowed to stir overnight at room temperature. Glycine (253 mg) in H$_2$O (2 mL) was then added dropwise and yellow cloudy mixture was stirred overnight at room temperature. The volatiles were evaporated in vacuo and the crude residue was diluted with H$_2$O (150 mL). The resulting white precipitate was collected by filtration then washed with H$_2$O (500 mL, 5×100 mL) to give a white solid. The solid was then dissolved in EtOAc (100 mL) and washed with 10 mM NaOH (3×100 mL) or until a colourless aqueous layer was achieved. The organic layer was washed with brine (100 mL), dried (MgSO$_4$), and concentrated to give product (312 mg, 62%) as a white solid. HPLC (5-70-90% MeCN, 0.1% TFA buffer; RT 18.3 min); LCMS (phobic method, formic buffer) RT=10.46 min; ESI MS (+ve) 1461.8 [M+3H]$^{3+}$/3-

3×Boc, 2341.9 [M+2H]$^{2+}$/2; [M+H]$^+$ 4681.8; calc. m/z for C$_{133}$H$_{252}$N$_{18}$O$_{47}$ [M+H]$^+$=4681.98. $^1$H-NMR (300 MHz, CD$_3$OD) δ (ppm): 1.21-1.81 (m, 232H); 2.63 (t, J 6.0 Hz, 2H); 3.00-3.15 (m, 29H); 3.34-3.40 (m, 7H); 3.57-3.87 (m, 94H); 4.06-4.36 (m, 14H); 6.54-6.84 (m, 8H); 7.95-8.17 (m, 12H);

viii. Azido-PEG$_{24}$-CO[N(PN)$_2$][Lys]$_8$[NH$_2$.TFA]$_{16}$ G3

To an ice-cooled, stirred suspension of N$_3$-PEG$_{24}$-CO[N (PN)$_2$][Lys]$_8$[Boc]$_{16}$ (167 mg) in water (4 mL) can be added TFA (6 mL). After 5 min, the ice-bath can be removed and the ensuing reaction mixture left to stir at room temperature overnight. The volatiles can be removed in vacuo and the remaining aqueous solution filtered through a 0.45 μm acrodisc syringe filter and purified by preparative HPLC.

ix. Azido-PEG$_{24}$-CO[N(PN)$_2$][Lys]$_8$[PEG]$_{16}$ G3

To a stirred solution of N$_3$-PEG$_{24}$-CO[N(PN)$_2$](Lys)$_8$ (NH$_2$.TFA)$_{16}$ (120 mg) and DIPEA (600 μL) in DMF (5 mL) at ambient temperature can be added NHS-PEG (2 equivalents per amine) The reaction mixture can be left to stir at ambient temperature for 16 h. The volatiles can be removed in vacuo and the resulting oil dissolved in MeCN/H$_2$O (5 mL, 1:1), filtered through a 0.45 μm acrodisc filter then purified by preparative HPLC;

x. Insulin-triazoloBCN-PEG$_{24}$-CO[N(PN)$_2$][Lys]$_4$[PEG$_{24}$]$_8$

The insulin BCN from Step B2 (3) can be combined with solid N$_3$-PEG$_{24}$-CO[N(PN)$_2$][Lys]$_4$[PEG$_{24}$]$_8$ (10 mg) and the ensuing mixture incubated at room temperature for 16 hours to afford the target molecule, which can be purified by preparative HPLC.

Example K Alternative Core i. N$_3$—PEG$_{24}$-CO[N(PN)$_2$][Lys (α-Boc)(ε-PEG$_{24}$)]$_4$ To a stirred solution of N$_3$-PEG$_{24}$-CO[N(PN)$_2$] [Lys]$_2$ [TFA]$_4$ (120 mg, 60.1 μmol) and DIPEA (335 μL, 1.92 mmol) in DMF (5 mL) at ambient temperature was added PyBOP (250 mg, 480 μmol). After 10 min, a solution of HO-Lys (α-Boc)(ε-PEG$_{24}$) (436 mg, 324 μmol) in DMF (5 mL) was added and the ensuing reaction mixture left to stir at ambient temperature for 16 h. The volatiles were removed in vacuo and the resulting oil dissolved in MeCN/H$_2$O (5 mL, 1:1), filtered through a 0.45 μm acrodisc filter then purified by preparative HPLC; 20-70% MeCN, 214 nm, to give a pale yellow oil (244 mg, 59%). LCMS (philic method, formic acid buffer) R$_t$=8.70 min ESI MS (+ve) 962 [M+ 7H]$^{7+}$/7, 1143 [M+6H]$^{6+}$/6, 1352 [M+5H]$^{5+}$/5, 1689 [M+ 4H]$^{4+}$/4. Transforms to 6852. $^1$H-NMR (300 MHz, CD$_3$OD) δ (ppm) 1.24-1.90 (m, 76H); 2.42-2.47 (m, 8H); 2.64 (broad t, J 6.3 Hz, 2H); 3.13-3.20 (m, 12H); 3.36 (s, 12H); 3.52-3.88 (m, 494H); 3.94-4.10 (m, 4H); 4.25-4.31 (m, 2H).

ii. N$_3$—PEG$_{24}$-CO[N(PN)$_2$][Lys (α-TFA)(ε-PEG$_{24}$)]$_4$

To an ice-cooled, stirred suspension of N$_3$-PEG$_{24}$-CO[N (PN)$_2$][Lys (α-Boc)(ε-PEG$_{24}$)]$_4$ (100 mg) in water (4 mL) was added TFA (6 mL). After 5 min, the ice-bath was removed and the ensuing reaction mixture left to stir at room temperature overnight. The volatiles were removed in vacuo and the remaining aqueous solution was filtered through a 0.45 μm acrodisc syringe filter and purified by preparative HPLC.

iv. Insulin-triazoloBCN-PEG$_{24}$-CO[N(PN)$_2$][Lys (α-TFA) (ε-PEG$_{24}$)]$_4$ The crude reaction mixture from step B2(3) above was then combined with solid N$_3$-PEG$_{24}$-CO[N(PN)$_2$][Lys(α-TFA)(ε-PEG$_{24}$)]$_4$ (7.7 mg, 1.11 μmol) and the ensuing mixture incubated at room temperature for 16 hours to afford a mixture of Insulin and the target molecule. LCMS (Philic method, formic acid buffer) R$_t$=7.75 min (Insulin), ESI MS 5808; R$_t$=8.40 min (Insulin-triazoloBCN-PEG$_{24}$-CO[N (PN)$_2$][Lys (α-TFA)(ε-PEG$_{24}$)]$_4$), MW=12439; ESI MS (+ve) 12437 (Max. Ent.)

FIGURES

FIGS. 1 to 6 and 8 to 9 show that the macromolecule of the present invention has an increased half-life and more prolonged action than existing long acting insulin detemir (in published studies, t½ of detemir ranges from 1.9-3.1 h and a CL/F of about 0.8-1.7 L/h/kg)

In published studies in healthy human volunteers, insulin detemir produced a linear and dose-proportional plasma insulin detemir concentration with a terminal half-life of five to seven hours, depending on the dose. The volume of distribution is approximately 0.1 L/kg and the bioavailability is 60%. The maximum serum insulin concentration is reached six to eight hours after subcutaneous administration. Because insulin detemir has an onset of action of 1 hour and a mean duration of action of 12 to 20 hours after administration of a 0.4-unit/kg dose, the drug may be administered once daily. In published clamp studies, Detemir showed a lower and later peak of action than NPL [GIR(max) 2.0 vs. 3.2 mg/kg/min, p<0.01; T(max) 9.1 (95% confidence interval: 3.0-14.7) vs. 7.0 h (1.8-15.2)].

The invention claimed is:
1. A macromolecule of Formula I:

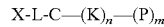

X-L-C—(K)$_n$—(P)$_m$   Formula I wherein
X represents a pharmaceutically active agent selected from the group consisting of insulin or an insulin analog and glucagon-like peptide (GLP) or a GLP analog or a GLP receptor agonist;
L represents a linker comprising polyethylene glycol (PEG) of between 20 and 36 monomer units;
C represents a core moiety having at least three functional groups each separately for attachment to L and attachment to at least two building units K, and wherein C is selected from a diamino or triamino moiety;
K represents a lysine or a lysine analog building unit having at least two branching points for attachment to a pharmacokinetic modifier P or another building unit K;
n is an integer from 30 to 126 and represents the total number of building units, and is a function of the number of generations and the extent of branching of the building units;
P represents a pharmacokinetic modifier comprising PEG or PEOX;
m is an integer from 32 to 128 and represents the number of surface pharmacokinetic modifiers,
wherein the total molecular weight of the surface pharmacokinetic modifiers constitutes 60-85% of the total molecular weight of the macromolecule, and
wherein the macromolecule has detectable activity in vivo for greater than 96 hours.

2. A macromolecule according to claim 1, wherein P comprises a branched or linear PEG of between about 1000 and 2500 Daltons.

3. A macromolecule according to claim 1, wherein the MW of the macromolecule is between about 15 kDa and 90 kDa.

4. A macromolecule according to claim 1, wherein X is insulin, L comprises PEG of 20 to 36 monomer units, C is a triamino compound, K comprises lysine, n is 30 to 126, P comprises PEG of 8 to 40 monomer units, and m is 32 to 128.

5. A pharmaceutical composition comprising a macromolecule according to claim 1 and a pharmaceutically acceptable excipient, carrier or adjuvant.

6. The pharmaceutical composition according to claim 5, with a concentration of X of at least 5 mg/ml of protein equivalent.

7. The pharmaceutical composition according to claim 5, with a concentration of X of at least 250 mg/ml of protein equivalent.

8. The pharmaceutical composition according to claim 5, wherein the concentration of insulin or insulin analogue is equal to or greater than about 100 U/ml.

9. The pharmaceutical composition according to claim 5, wherein the concentration of insulin or insulin analogue is equal to or greater than about 4000 U/ml.

10. The pharmaceutical composition according to claim 9, with viscosity below 50 cP.

11. The pharmaceutical composition according to claim 5, wherein the macromolecule is stable at room temperature for greater than 6 months.

12. The pharmaceutical composition according to claim 5, wherein the macromolecule has detectable activity in vivo for greater than 168 hours.

13. The pharmaceutical composition according to claim 5, wherein the macromolecule is suitable for weekly administration to a subject.

14. The pharmaceutical composition according to claim 5, wherein the macromolecule is suitable for fortnightly administration to a subject.

15. A method for providing an extended plasma residence time for a pharmaceutically active agent, comprising administering the macromolecule of claim 1 to a subject in need thereof wherein said macromolecule provides for an extended plasma residence time for the pharmaceutically active agent in the subject.

16. The method according to claim 15, wherein the pharmacokinetic profile of X is improved compared to unconjugated X, by at least 10% increase in AUC.

17. The method according to claim 15, wherein the pharmacokinetic profile of X is improved compared to unconjugated X, by at least 200% increase in AUC.

18. The method according to claim 15, wherein the T½ is 12 to 52 hours.

19. A method for providing single daily or weekly dosing of a pharmaceutically agent, the method comprising administering a pharmaceutical composition comprising the macromolecule of claim 1 to a subject in need thereof, wherein said macromolecule provides for single daily or weekly dosing of the pharmaceutically active agent X.

20. The method according to claim 19, wherein the volume of pharmaceutical composition administered is less than 1 ml, or less than 500 ul or 250 ul.

21. The method according to claim 19, wherein the pharmaceutically active agent X is insulin or an insulin analogue, for the treatment of hyperglycemia, diabetes mellitus, or gestational diabetes.

22. A method of treatment of hyperglycemia, diabetes mellitus, or gestational diabetes, in a subject by administration to the subject in need of treatment thereof a macromolecule according to claim 1, wherein the pharmaceutically active agent X is insulin or an insulin analogue.

23. The method according to claim 22, wherein the macromolecule wherein the macromolecule has detectable activity in vivo for greater than 168 hours.

24. The method according to claim 22, wherein the macromolecule is administered weekly.

25. The method according to claim 22, wherein the macromolecule is administered fortnightly.

26. A macromolecule according to claim 1, wherein the macromolecule has detectable activity in vivo for greater than 168 hours.

27. A macromolecule according to claim 1, wherein the macromolecule is suitable for weekly administration to a subject.

28. A macromolecule according to claim 1, wherein the macromolecule is suitable for fortnightly administration to a subject.

29. A macromolecule according to claim 1, wherein X is insulin, L comprises PEG of 24 monomer units, C is a triamino compound, K comprises lysine, n is 62, P comprises PEG of 8 monomer units, and m is 64.

30. A macromolecule according to claim 1, wherein X is insulin, L comprises PEG of 20 monomer units, C is a triamino compound, K comprises lysine, n is 30, P comprises PEG of trident (4+3×4) monomer units, and m is 32.

31. A macromolecule according to claim 1, wherein X is insulin, L comprises PEG of 36 monomer units, C is a triamino compound, K comprises lysine, n is 126, P comprises PEG of 8 monomer units, and m is 128.

32. A macromolecule according to claim 1, wherein X is insulin, L comprises PEG of 24 monomer units, C is a triamino compound, K comprises lysine, n is 62, P comprises PEG of 24 monomer units, and m is 64.

* * * * *